United States Patent [19]
McGuire et al.

[11] Patent Number: 5,188,964
[45] Date of Patent: Feb. 23, 1993

[54] METHOD AND KIT FOR THE PROGNOSTICATION OF BREAST CANCER PATIENT VIA HEAT SHOCK/STRESS PROTEIN DETERMINATION

[75] Inventors: William L. McGuire; Atul K. Tandon; Gary M. Clark; Gary C. Chamness, all of San Antonio, Tex.

[73] Assignee: Board of Regents, The University of Texas System, Austin, Tex.

[21] Appl. No.: 509,377

[22] Filed: Apr. 12, 1990

[51] Int. Cl.$^5$ ............................................. G01N 33/48
[52] U.S. Cl. ........................................ 436/64; 422/61; 436/63; 436/501; 252/408.1; 435/7.23
[58] Field of Search ............................ 436/64, 63, 501; 435/287, 288, 810, 960, 975, 7.23; 252/408.1; 422/61

[56] References Cited
PUBLICATIONS

International Search Report.
G. C. Chamness et al., "Estrogen-inducible heat shock protein hsp27 predicts recurrence in node-negative breast cancer," Proceedings of the American Assoc. for Cancer Research (1989) 30:252.
Ahmed Berrada et al., (Oct. 1990) "Glucocorticoid Effects and Receptors in Two Rat Colon Carcinoma Cell Lines Differing by their Tumorigenicity," J. of Steroid Biochem. & Molec. Biol. 37:223–230.
Kyu Seong Kim et al., (Feb. 1990) "Expression of the Glucose-Regulated Proteins (GRP94 and GRP78) in Differentiated and Undifferentiated Mouse Embryonic Cells and the Use of the GRP78 Promoter as an Expression System in Embryonic Cells," Differentiation, 42:153–159.
Suzanne A. W. Fuqua et al., (Aug. 1, 1989) "Induction of the Estrogen-Regulated 24K Protein by Heat Shock," Cancer Research 49:4126–4129.
Ralph Buttyan et al., (1988) "Cascade Induction of c-fos, c-myc, and Heat Shock 70K Transcripts During Regression of the Rat Ventral Prostate Gland," Molecular Endocrinology 2:650–657.
Tomasovic and Welch, "Heat Stress Proteins and Experimental Cancer Metastasis," Int. J. Hyperthermia, 2:253–66 (1986).
Ritossa, F., "A New Puffing Pattern Induced by Temperature Shock and DNP in Prosophila," Experientia, 18:571–573 (1962).
Tissieres et al., "Protein Synthesis in Salivary Glands of Drosophila melangogaster: Relation to Chormosome Puffs," J. Mol. Biol., 84:389–398 (1974).
Lindquist et al., "The Heat-Shock Proteins," Annu. Rev. Genet., 631–77 (1988).
Schlesinger et al., "Heat Shock Proteins: The Search for Functions," J. of Cell Biol., 103:321–325 (1986).
Pelham, "Speculations on the Functions of the Major Heat Shock and Glucose-Regulated Proteins," Cell 46:959–961 (1986).
Craig, "The Heat Shock Response," CRC Crit. Rev. in Biochem., vol. 18, Issue 3:239–280.
Edwards et al., "Estrogen Induced Synthesis of Specific Proteins in Human Breast Cancer Cells," Biochem. and Biophys. Res. Com., vol. 93, No. 3:804–812 (1980).
Adams et al., "Detection of a $M_r$ 24,000 Estrogen-Regulated Protein in Human Breast Cancer by Monoclonal Antibodies[1]," Cancer Research 43:4297–4301 (1983).

(List continued on next page.)

Primary Examiner—James C. Housel
Assistant Examiner—William Chan
Attorney, Agent, or Firm—Arnold, White & Durkee

[57] ABSTRACT

The invention relates to a method of predicting disease-free survival in cancer patients by relating the number and amount of stress response proteins in the cancer tissue to the probability of tumor recurrence. Particular heat shock/stress response proteins useful in the determination of tumor recurrence are the stress response proteins, hsp70, hsp90, hsp27, and glucose regulated protein grp94. Specific levels of the stress response proteins are identified, above which the probability of tumor recurrence is highly signficant. Kit methods are disclosed which could enable determination of the stress proteins by an antibody assay.

24 Claims, 6 Drawing Sheets

PUBLICATIONS

Hickey et al., "Sequence and Organization of Genes Encoding the Human 27 kDa Heat Shock Protein," Nucleic Acids Research, vol. 14, No. 10:4127–4145 (1986).

McGuire et al., "Chromosomal Assignments of Human 27-kDa Heat Shock Protein Gene Family," Som. Cell and Mol. Gen., vol. 15, No. 2:167–171 (1989).

Chamness et al., "Stress Response Protein srp27 Predicts Recurrence in Node–Negative Breast Cancer," BCRT 12:130 (1988).

Brugge et al., "The Specific Interaction of the Rous Sarcoma Virus Transforming Protein, pp60$^{src}$, with Two Cellular Proteins", Cell, 25:363–372 (1981).

Oppermann et al., "A cellular protein that associates with the transforming protein of Rous sarcoma virus is also a heat–shock protein," Proc. Natl. Acad. Sci. USA, vol. 78, No. 2:1067–1071 (1981).

Adkins et al., "The Transforming Proteins of PRCII Virus and Rous Sarcoma Virus Form a Complex with the Same Two Cellular Phosphoproteins," Jour. of Virology, vol. 43, No. 2:448–455 (1982).

Lipsich et al., "Association of the Transforming Proteins of Rous, Fujinami, and Y73 Avian Sarcoma Viruses with the Same Two Cellular Proteins," Mol. and Cell. Bio., vol. 2, No. 7:875–880 (1982).

Ziemiecki, "Characterization of Monomeric and Complex–Associated Forms of the gag–onc Fusion Proteins of Three Isolates of Feline Sarcoma Virus: Phosphorylation, Kinase Activity, Acylation, and Kinetics of Complex Formation," Virology, 151:265–273 (1986).

Rose et al., "The 90-Kilodalton Peptide of the Heme-Regulated eIF-2$\alpha$ Kinase Has Sequence Similarity with the 90–Kilodalton Heat Shock Protein," Biochemistry 26:6583–6587 (1987).

Catelli et al., "Definition of Domain of HSP 90 Interacting with Receptors," J. Cell. Biochem. Supplements 12D:276.

Dougherty et al., "Polypeptide Components of Two 8 S Forms of Chicken Oviduct Progesterone Receptor," J. Biochem. 259(12): 8004–8009 (1984).

Joab et al., "Common Non–hormone Binding Component in Non–transformed Chick Oviduct Receptors of Four Steroid Hormones," Nature 308:850–853 (1984).

Redeuilh et al., "Subunit Composition of the Molybdate-Stabilized '8-9S' Nontransformed Estradiol Receptor Purified from Calf Uterus," J. Biochem. 262(15):6969–6975 (1987).

Renoir et al., "Involvement of a Non–Hormone–Binding 90–Kilodalton Protein in the Nontransformed 8S Form of the Rabbit Uterus Progesterone Receptor," Biochem. 25:6405–6413 (1986).

Sanchez et al., "The Molybdate-Stabilized Glucocorticoid Binding Complex of L-Cells Contains a 98-100 KDalton Nonsteroid Phosphoprotein and a 90 KDalton Nonsteroid-Binding Phosphoprotein That Is Part of the Murine Heat-Shock Complex," J. Steroid Biochem. 24(1):9–18 (1986).

Sanchez et al., "Relationship of the 90-kDa Murine Heat Shock Protein to the Untransformed and Transformed States of the L Cell Glucocorticoid Receptor," J. Biochem. 262(15):6986–6991 (1987).

Koyasu et al., "Two Mammalian Heat Shock Proteins, HSP90 and HSP100, Are Actin-Binding Proteins," Proc. Natl. Acad. Sci. 83:8054–8058 (1986).

Nishida et al., "Calmodulin–regulated Binding of the 90–kDa Heat Shock Protein to Actin Filaments," J. Biochem. 261(34):16033–16036 (1986).

Welch and Suhan, "Morphological Study of the Mammalian Stress Response: Characterization of Changes in Cytoplasmic Organelles, Cytoskeleton, and Nucleoli, and Appearance of Intranuclear Actin Filaments in Rat Fibroblasts after Heat-Shock Treatment," J. Cell Biol. 101:1198–1211 (1985).

Sanchez et al., "Demonstration That the 90-kDa Heat Shock Protein Is Associated with Tubulin in L–Cell Cytosol and in Intact PtK Cells," J. Cell Biochem. Supplements 12D:283.

Ullrich et al., "A Mouse Tumor-Specific Transplantation Antigen Is A Heat Shock–Related Protein," Proc. Natl. Acad. Sci. 83:31221–3125 (1986).

Goate et al., "Localization of a Human Heat–Shock HSP 70 Gene Sequence to Chromosome 6 and Detection of Two Other Loci by Somatic–Cell Hybrid and Restriction Fragment Length Polymorphism Analysis," Hum. Genet. 75:123–128 (1987).

Harrison et al., "Chromosomal Location of Human Genes Encoding Major Heat-Shock Protein HSP70," Somatic Cell and Mol. Genet. 13(2):119–130 (1987).

Chappell et al., "Uncoating ATPase Is a Member of the 70 Kilodalton Family of Stress Proteins," Cell 45:3–13 (1986).

(List continued on next page.)

PUBLICATIONS

Welch and Feramisco, "Rapid Purification of Mammalian 70,000–Dalton Stress Proteins: Affinity of the Proteins for Nucleotides," Mol. and Cell. Biol. 5(6):1229–1237.

Zylicz et al., "The dnaK Protein of *Escherichia coli* possesses an ATPase and Autophosphorylating Activity and Is Essential in an in vitro DNA Replication System," Proc. Natl. Acad. Sci. 80:6431–6435 (1983).

Milarski and Morimoto, "Expression of Human HSP70 During the Synthetic Phase of the Cell Cycle," Proc. Natl. Acad. Sci. 83:9517–9521 (1986).

Wu and Morimoto, "Transcription of the Human HSP70 Gene Is Induced By Serum Stimulation," Proc. Natl. Acad. Sci. 82:6070–6074 (1985).

Nevins, Joseph R., "Induction of the Synthesis of a 70,000 Dalton Mammalian Heat Shock Protein by the Adenovirus E1A Gene Product," Cell 29:913–919 (1982).

Welch and Suhan, "Cellular and Biochemical Events in Mammalian Cells During and After Recovery from Physiological Stress," J. Cell Biol. 103:2035–2052 (1986).

Pelham, Hugh R. B., "Hsp 70 Accelerates the Recovery of Nucleolar Morphology After Heat Shock," The EMBO Journal 3(13):3095–3100 (1984).

Lewis and Pelham, "Involvement of ATP in the Nuclear and Nucleolar Functions of the 70 kd Heat Shock Protein," The EMBO Journal 4(12):3137–3143 (1985).

Rothman and Schmid, "Enzymatic Recycling of Clathrin from Coated Vesicles," Cell, 48:5–9 (1986).

Ungewickell, Ernst, "The 70-kd Mammalian Heat Shock Proteins Are Structurally and Functionally related to the Uncoating Protein that Release Clathrin Triskelia from Coated Vesicles," The EMBO Journal 4(13A):3385–3391 (1985).

Bardwell and Craig, "Major Heat Shock Gene of Drosophila and the *Eschericia coli* Heat-Inducible dnaK Gene are Homologous," Proc. Natl. Acad. Sci. 81:848–852 (1984).

LeBowitz et al., "Initiation of DNA Replication on Single-Stranded DNA Templates Catalyzed by Purified Replication Proteins of Bacteriophage λ and *Escherichia coli*," Proc. Natl. Acad. Sci. 82:3988–3992 (1985).

Dodson et al., "Specialized Nucleoprotein Structures at the Origin of Replication of Bacteriophage λ: Complexes with λ O Protein and with λ O, λ P, and *Escherichia coli* DnaB Proteins," Proc. Natl. Acad. Sci. 82:4678–4682 (1985).

Pinhasi-Kimhi et al., "Specific Interaction Between the p53 Cellular Tumour Antigen and Major Heat Shock Proteins," Nature 320:182–185 (1986).

Finlay et al., "Activating Mutations for Transformation by p53 Produce a Gene Product That Forms an hsc70–p53 Complex with an Altered Half-Life," Mol. and Cell. Biol. 8(2):531–539 (1988).

Clarke et al., "Purification of Complexes of Nuclear Oncogene p53 with Rat and *Eschericia coli* Heat Shock Proteins: In Vitro Dissociation of hsc70 and dnaK from Murine p53 by ATP," Mol. and Cell. Biol. 8(3):1206–1215 (1988).

Notarianni and Preston, "Activation of Cellular Stress Protein Genes by Herpes Simplex Virus Temperature-Sensitive Mutants Which Overproduce Immediate Early Polypeptides," Virology 123:113–122 (1982).

Khandjian and Türler, "Simian Virus 40 and Polyoma Virus Induce Synthesis of Heat Shock Proteins in Perimissive Cells," Mol. and Cell. Biol. 3(1):1–8 (1983).

Collins and Hightower, "Newcastle Disease Virus Stimulates the Cellular Accumulation of Stress (Heat Shock) mRNAs and Proteins," J. Virology 44(2):703–707 (1982).

Mitchell et al., "Self-Degradation of Heat Shock Proteins," Proc. Natl. Acad. Sci. 82:4969–4973 (1985).

Lee et al., "Biochemical Characterization of the 94- and 78-kilodalton Glucose-Regulated Proteins in Hamster Fibroblasts," J. Biochem. 259(7):4616–4621 (1984).

Shiu et al., "Glucose Depletion Accounts for the Induction of Two Transformation-Sensitive Membrane Proteins in Rous Sarcoma Virus-Transformed Chick Embryo Fibroblasts," Proc. Natl. Acad. Sci. 74(9):3840–3844 (1977).

Chang et al., "Rat Gene Encoding the 78-kDa Glucose-Regulated Protein GRP78: Its Regulatory Sequences and the Effect of Protein Glycosylation on Its Expression," Proc. Natl. Acad. Sci. 84:680–684 (1987).

Lin et al., "A Calcium Ionophore-Inducible Cellular Promoter is Highly Active and Has Enhancerlike Properties," Mol. and Cell. Biol. 6(4):1235–1243 (1986).

(List continued on next page.)

OTHER PUBLICATIONS

Munro and Pelham, "An Hsp70-like Protein in the ER: Identity with the 78kD Glucose-Regulated Protein and Immunoglobulin Heavy Chain Binding Protein," Cell 46:291-300 (1986).

Bole et al., "Posttranslational Association of Immunoglobulin Heavy Chain Binding Protein with Nascent Heavy Chains in Nonsecreting an Secreting Hybridomas," 102:1558-1566 (1986).

Gething et al., "Expression of Wild-Type and Mutant Forms of Influenza Hemagglutinin: The Role of Folding in Intracellular Transport;" Cell 46:939-950 (1986).

Sorge and Pelham, "The Glucose-Regulated Protein grp94 Is Related to Heat Shock Protein Hsp90," J. Mol. Biol. 194:341-344 (1987).

Bloemendal et al., "The State of Aggregation of $\alpha$-Crystallin Detected after Large-Scale Preparation by Zonal Centrifugation," Eur. J. Biol. Chem. 24:401-406 (1972).

Ingolia and Craig, "Four Small Drosophila Heat Shock Proteins are Related to Each Other and to Mammalian $\alpha$-Crystallin," Proc. Natl. Acad. Sci. 79:2360-2364 (1982).

Collier and Schlesinger, "The Dynamic State of Heat Shock Proteins in Chicken Embryo Fibroblasts," J. Cell Biol. 103:1495-1507 (1986).

Nover et al., "Formation of Cytoplasmic Heat Shock Granules in Tomato Cell Cultures and Leaves," Mol. and Cell. Biol. 3(9):1648-1655 (1983).

Chin et al., "Heat Shock and Arsenite Increase Expression of the Multidrug Resistance (MDR1) Gene in Human Renal Carcinoma Cells," J. Biol. Chem. 265(1):221-226 (1990).

Shen et al., "Coinduction of Glucose-regulated Proteins and Doxorubicin Resistance in Chinese Hamster Cells," Proc. Natl. Acad. Sci. 84:3278-3282 (1987).

Clark et al., "Progesterone Receptors as a Prognostic Factor in Stage II Breast Cancer," New England J. Medicine 309:1343-1347 (1983).

Dressler et al., "DNA Flow Cytometry and Prognostic Factors in 1331 Frozen Breast Cancer Specimens," Cancer 61(3):420-427 (1988).

Clark et al., "Prediction of Relapse or Survival in Patients with Node-Negative Breast Cancer by DNA Flow Cytometry," New England J. Medicine 320:627-633 (1989).

Bevilacqua et al., "Association of Low nm23 RNA Levels in Human Primary Infiltrating Ductal Breast Carcinomas with Lymph Node Involvement and Other Histopathological Indicators of High Metastatic Potential," Cancer Res. 49:5185-5190 (1989).

Tandon et al., "HER-2/neu Oncogene Protein and Prognosis in Breast Cancer," J. Clinical Oncology 7(8):1120-1128 (1989).

Tandon et al., "Cathespin D and Prognosis in Breast Cancer," New England J. Medicine 322:297-302 (1990).

Edwards et al., "Structural Analysis of Chicken Oviduct Progresterone Receptor Using Monoclonal Antibodies to the Subunit B Protein," Biochemistry 23(19):4427-4435 (1984).

Sargan et al., "hsp108, a Novel Heat Shock Inducible Protein of Chicken," Biochemistry 25:6252-6258 (1986).

Schuh et al., "A 90,000-Dalton Binding Protein Common to Both Steroid Receptors and the Rous Sarcoma Virus Transforming Protein, $pp60^{v-src*}$," J. Biol. Chem. 260(26):14292-14296 (1985).

McGuire et al., "Evaluation of Estrogen Receptor Assays in Human Breast Cancer Tissue," Cancer Research 37:637-639 (1977).

Powell et al., "Measurement of Progesterone Receptor in Human Breast Cancer Biopsies," Cancer Research 39:1678-1682 (1979).

Breslow, N. E., "Analysis of Survival Data Under the Proportional Hazards Model," Int. Stat. Rev. 43(1):45-58 (1975).

Cox, D. R., "Regression Models and Life-Tables," J. R. Statist. Soc. 4(2):187-220 (1972).

Kalbfleisch and Prentice, *The Statistical Analysis of Failure Time Data* (John Wiley and Sons, New York, 1980).

Smith et al., "Measurement of Protein Using Bicinchoninic Acid," Analytical Biochemistry 150:76-85 (1985).

Kaplan and Meir, "Nonparametric Estimation From Incomplete Observations," American Statist. Assoc. J. 457-481 (Jun. 1958).

Mantel, Norman, "Evaluation of Survival Data and Two New Rank Order Statistics Arising in Its Consideration," Cancer Chemotherapy Reports 50(3):163-170 (1966).

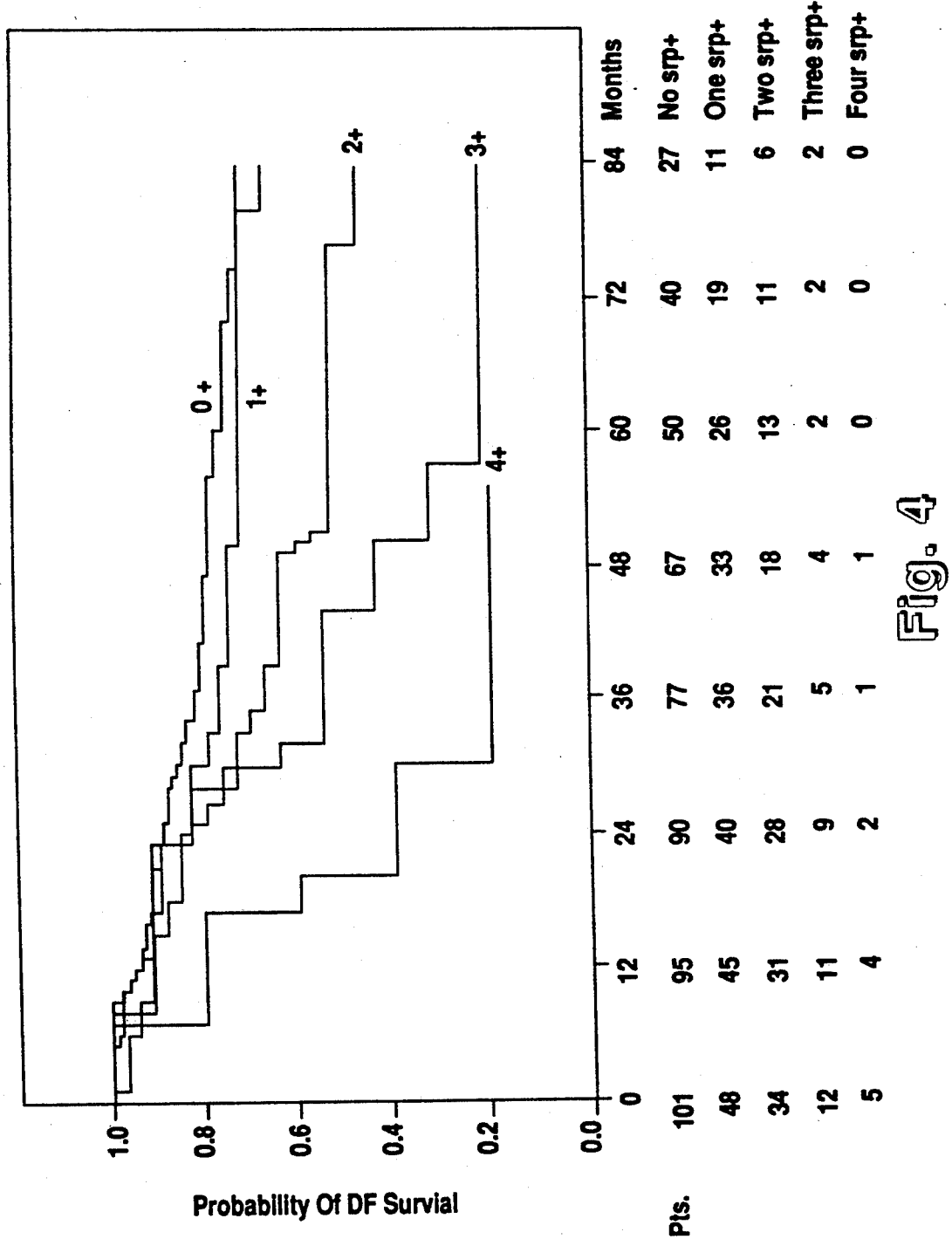

METHOD AND KIT FOR THE PROGNOSTICATION OF BREAST CANCER PATIENT VIA HEAT SHOCK/STRESS PROTEIN DETERMINATION

This work was supported in part by a research grant from the National Cancer Institute. The United States Government may have certain rights in the claimed invention including a paid-up license in the invention and the right in limited circumstances to require the patent owner to license others on reasonable terms as provided for by the terms of grant No. CA 11378 awarded by the National Cancer Institute.

BACKGROUND OF THE INVENTION

1. Field of the Invention

The invention relates to a method of predicting disease-free survival probability in cancer patients. In particular, the method enables prediction of tumor recurrence in node-negative breast cancers as related to the levels and the number of stress response proteins in primary tumors.

2. Description of Related Art

Stress response proteins, srp's, have been recognized for several years, although in earlier terminology they were commonly called heat shock proteins, hsp's, because they were originally discovered as families of related proteins rapidly overproduced in divergent species in response to temperature stress. Subsequently these proteins were found to be induced in response to a variety of environmental stresses, including stimuli such as heat, heavy metals, toxins, drugs, hypoxia, and alcohol.

The precise function of stress response proteins is still largely a matter of speculation. It is widely assumed that these proteins protect cells from the effects of stress, but little is known about the mechanisms of induction and even less is understood about the relationships between number and amount of protein induced and the underlying physiological phenomenon.

There have been speculations that pretumorous or tumor cells might express increased amounts of stress response proteins, leading some workers to search for a relation between levels of these proteins and tumor manifestation. But although readily induced, the higher levels of heat stress proteins did not appear to relate to increased probability of tumor recurrence; in fact, some studies indicated that metastatic tumor burden generally decreased following induction of stress proteins (S. P.. Tomasovic and D. R. Welch, *Hyperthermia* 2, 253 (1986)). Subsequent work by McGuire and colleagues, however, demonstrated that an estrogen-induced protein found in MCF-7 human breast cancer cells was identical to one of the earlier discovered heat shock proteins, hsp27, and that hsp27 might be associated with node-negative breast cancer patients at high risk of recurrence. Nevertheless, correlation factors were relatively weak and not sufficient to suggest a clinically useful method of prognostication.

The phenomenon of heat shock response was first observed nearly three decades ago by Ritossa (F. Ritossa, *Experientia* 18, 571 (1962)) who found that an increase in temperature from 20° to 37° C., as well as exposure to certain chemicals such as dinitrophenol or sodium salicylate, leads to a remarkable change in the puffing pattern of polytene chromosomes in salivary glands of fruit flies (*Drosophila hydei*). Nearly 12 years after this observation, Tissieres et al. (A. Tissieres, H. K. Mitchell, U. M. Tracy, *J. Mol. Biol.* 84, 389 (1974)) reported the induction of a set of proteins called heat shock proteins (hsp's), as a consequence of heat shock. Today, practically all types of organisms are known to respond to an increase in temperature in a basically similar fashion by massive synthesis and accumulation of a group of hsp's with almost no tissue or cell type specificity. Major hsp's are now known to be very highly conserved through evolution, strongly suggesting their vital role in survival of the organisms. Nearly all species induce the synthesis of proteins in the size ranges of 80 to 90 kDa, 68 to 74 kDa, and 18 to 30 kDa. In the past few years, the genes encoding the hsp's have been isolated and through sequence analysis have been placed into three "universal" families. These are known by their molecular weights: hsp90, hsp70, and hsp27 (the exact molecular weight differs slightly from organism to organism). These hsp genes contain a conserved sequence of 14 base pairs in the 5' noncoding region, the Pelham box, which serves as the promoter for hsp mRNA transcription. Recently, a relationship between the sequences of hsp's and another family of stress proteins, the glucose-regulated proteins (grp's), has been reported. These proteins are oversynthesized in response to glucose starvation. Two major grp's have been identified as grp94 and grp78.

Although the precise function of stress response proteins (srp's) is not known, they are thought to be intimately involved in enhancing the cell's ability to recover from stress (e.g. conferring thermotolerance). Yet the exact biochemical mechanism of this protection of cells against physical and chemical environmental insults remains a mystery. There are several excellent and comprehensive reviews on this subject including the organization and regulation of expression of hsp genes (S. Linquist, E. A. Craig, *Ann. Rev. Genet.* 22, 631 (1988) M. J. Schlesinger, *J. Cell Biol.* 103, 321 (1986); H.R.B. pelham, *Cell* 46, 959 (1988); E. A. Craig, *CRC Crit. Rev. Biochem.* 18, 239 (1985)).

In 1980, a cytoplasmic, estrogen-induced protein of 24,000–28,000 Daltons molecular weight (termed "24K") in MCF-7 human breast cancer cells (D. P. Edwards, D. J. Adams, N. Savage, W. L. McGuire, *Biochem. Res. Commun.* 93, 804 (1980)) was reported. Its relative abundance in estrogen-stimulated MCF-7 cells enabled researchers to rapidly develop a highly specific monoclonal antibody against it (D. J. Adams, H. Hajj, D. P. Edwards, R. J. Bjercke, W. L. McGuire, *Cancer Res.* 43, 4297 (1983)). Nucleotide and deduced amino acid sequence of "24K" (S. A. W. Fuqua, M. B. Salingaros, W. L. McGuire, ibid. 49, 4126 (1989)) revealed its identity to the low molecular weight human heat shock protein hsp27, earlier reported in HeLa cells (E. Hickey et al., *Nucleic Acid Res.* 14, 4127 (1986)). Somatic cell hybridization showed that it is a multigene family, located on three different chromosomes namely 3,9 and X (S. McGuire, S. A. W. Fuqua, S. L. Naylor, D. A. Helen-Davis, W. L. McGuire, *Somatic Cell Genet.* 15, 167 (1989)). It is dually induced by heat shock as well as by estrogen in MCF-7 cells. A study of its possible significance for predicting clinical outcome showed that it was a factor for defining node-negative breast cancer patients at high risk of recurrence (G. C. Chamness, A. Ruiz, L. Fulcher, G. M. Clark, W. L. McGuire, *Breast Cancer Res. Treat.* 12, 130 (1988) (Abstract #94); G. C. Chamness et al., *Proc. Am. Assoc. Cancer Res.* 30, 252 (1989)) (Abstract #1002).

The heat shock protein hsp90 is known to interact with several protein-tyrosine kinases between the time of their synthesis and their ultimate association with the plasma membrane. The transforming protein of Rous Sarcoma Virus, pp60$^{src}$, was the first tyrosine kinase with which hsp90 was shown to have a specific association (J. S. Brugge, E. Erikson, R. L. Erikson, *Cell* 25, 363 (1981); H. Oppermann, W. Levinson, J. M. Bishop, *Proc. Natl. Acad. Sci.* 78, 1067 (1981)). Other transforming proteins with tyrosine kinase activity, yes, fps, fes, and fgr, also form stable complexes with a 90 kDa protein. In some cases this 90 kDa protein has been identified as hsp90 (B. Adkins, T. Hunter, B. M. Sefton, *J. Virol.* 43, 448 (1982); L. A. Lipsich, J. R. Cutt, J. S. Brugge, *Mol. Cell Biol.* 2, 875 (1982); and A. Ziemiecki, *Virology* 151, 265 (1986)). It has been proposed that hsp90 transports and modulates these kinases by forming soluble, inactive complexes. Hsp90 has also been found associated with other cellular kinases, e.g. heme-controlled eIF2-alpha kinase and casein kinase II (D. W. Rose, R. E. H. Wettenhall, W. Kudlicki, G. Kramer, B. Hardesty, *Biochemistry* 26, 6583 (1987)).

All steroid hormone receptors, including the estrogen, progesterone, and glucocorticoid receptors, can be isolated in the inactivated state (i.e.. in the absence of steroid hormones) as approximately 300 kDa complexes, which in addition to the specific hormone-binding proteins, contain 90 kDa proteins that have now been identified as hsp90 (M. G. Catelli, C. Radanyi, J. M. Renoir, N. Binart, E. E. Baulieu, *J. Cell Biochem.* Suppl. 12D. 286 (1988); J. J. Dougherty, R. K. Puri, D. O. Toft, *J. Biol. Chem.* 259, 8004 (1984); I. Joab, et al., *Nature* 308, 850 (1984); G. Redeuilh, B. Moncharmont, C. Secco, E.-E. Baulieu, *J. Biol. Chem.* 262, 6969 (1987); J.-M. Renoir, T. Buchou, E.-E. Baulieu, *Biochemistry* 25, 6405 (1986); and E. R. Sanchez, P. R. Housley, W. B. Pratt, *J. Steroid Biochem.* 24, 9 (1986)). Dissociation of hsp90 from the complex leads to the activation of the receptor for DNA binding (I. Joab, et al., *Nature* 308, 850 (1984); J.-M. Renoir, T. Buchou, E.-E. Baulieu, *Biochemistry* 25, 6405 (1986); and E. R. Sanchez, et al., *J. Biol. Chem.* 262, 6986 (1987)). In the absence of hsp90, the hormone-binding receptor will bind to the DNA whether hormone is present or not (E. R. Sanchez, et al., *J. Biol. Chem.* 262, 6986 (1987)). Hsp90 itself binds neither DNA nor hormone. Apparently, binding of hsp90 to the receptor prevents the receptor from binding to DNA until hormone disrupts association of hsp90 to the receptor.

In broad outline, hsp90 appears to play a role in steroid receptor complexes similar to that in tyrosine kinase complexes, keeping the receptor inactive until the proper signal for activation is received.

Recently, hsp90 has also been reported to associate with actin in lymphocyte extracts, in a manner dependent on calcium and regulated by calmodulin (S. Koyasu, et al., *Proc. Natl. Acad. Sci. USA* 83, 8054 (1986); and E. Nishida, S. Koyasu, H. Sakai, I. Yahara, *J. Biol. Chem.* 261, 16033 (1986)). It has been postulated that the actin association provides a mechanism for transport of hsp90. In this regard, and considering the tendency of hsp90 to move into the nucleus with heat shock, it is notable that actin filaments rearrange during heat shock and may even be found in substantial quantities in the nuclei of heat-shocked cells (W. J. Welch, J. P. Suhan, *J. Cell Biol.* 101, 1198 (1985)). Hsp90 also appears to be associated with tubulin both in vitro and in vivo (E. H. Bresnick, T. Redmond, E. R. Sanchez, W. B. Pratt, M. J. Welsh, *J. Cell Biochem.* Suppl. 12D, 283 (1988)). Given the high concentrations of actin, tubulin, and hsp90 in the cell, these associations may be biologically significant.

A tumor-specific transplantation antigen, Meth A, has also recently been identified as hsp90 (S. J. Ullrich, E. A. Robinson, L. W. Law, M. Willingham, E. Apella, *Proc. Natl. Acad. Sci. USA* 83, 121 (1986)).

In humans, the heat shock protein hsp70 represents a multigene family, located on chromosomes 6, 14, 21, and at least one other chromosome (A. M. Goate, et al., *Hum. Genet.* 75, 123 (1987); and G. S. Harrison, et al., *Somatic Cell Mol. Genet.* 13, 119 (1987)). Their protein products are present in different cellular compartments and are often associated with other proteins. All bind ATP with high affinity (T. G. Chappell, et al., *Cell* 45, 3 (1986); W. J. Welch, J. R. Feramisco, *Mol. Cell. Biol.* 5, 1229 (1985); and M. Zylicz, J. H. LeBowitz, R. McMacken, C. P. Georgopoulos, *Proc. Natl. Acad. Sci. USA* 80, 6431 (1983)) and are implicated in a number of cellular processes. The major hsp70 is a cell cycle regulated protein (K. L. Milarski, R. Morimoto, *Proc. Natl. Acad. Sci. USA* 83, 9517 (1986)), is serum stimulated (B. J. Wu, R. I. Morimoto, *Proc. Natl. Acad. Sci. USA* 82, 6070 (1985)), and is induced by adenovirus EIA protein (J. R. Nevins, *Cell* 29, 913 (1982)).

It seems that the cell exploits a general property of the hsp70 family, namely the ability to disrupt protein-protein interactions, to perform specific tasks. Most of the "reactions" involving proteins of the hsp70 family require ATP. Probably the disruption of the protein-protein interactions uses the energy released on ATP hydrolysis.

One function of hsp70 may be the repair of damaged cells. Very shortly following heat shock, hsp70 translocates from cytoplasm to nucleus changing from a "soluble" cytosolic to an "insoluble" nuclear-matrix form. In the nucleus it subsequently concentrates in nucleoli where it apparently binds to partially assembled ribosomes (W. J. Welch, J. P. Suhan, *J. Cell Biol.* 103, 2035 (1986)). Nucleoli are very sensitive to thermal damage, but transfection of cells with a plasmid that overproduces hsp70 accelerates their recovery from heat shock (H.R.B. Pelham, *EMBO J* 3, 3095 (1984)), indicating that hsp70 binds to denatured or abnormal proteins after heat shock to prevent their aggregation and thus to prevent cellular damage. Hsp70 is rapidly and completely released from "insoluble" nuclear matrix on addition of ATP (M. J. Lewis, H. R. B. Pelham, *EMBO J* 4, 3137 (1985)). This observation led Lewis and Pelham (M. J. Lewis, H.R.B. Pelham, *EMBO J* 4, 3137 (1985)) to propose that hsp70 binds to denatured, aggregated proteins and solubilizes them. Energy from ATP hydrolysis subsequently causes hsp70 to release, thereby allowing the proteins to refold.

Clathrin-uncoating ATPase has been identified as a member of the hsp70 gene family. In the presence of ATP, an hsp70-like protein binds to the clathrin cages and is induced to hydrolyze ATP, resulting in the disruption of clathrin-clathrin interactions and finally in disassembly of the cage into clathrin trimers (J. E. Rothman, S. L. Schmid, *Cell* 46, 5 (1986); T. G. Chappell, et al., *Cell* 45, 3 (1986); and E. Ungewickell, *EMBO J* 4, 3385 (1985)).

In E. coli, hsp70 is the product of the dnak gene, which encodes a protein that is 50% identical in amino acid sequence to hsp70 of eukaryotes (J. C. A. Bardwell, E. A. Craig, *Proc. Natl. Acad. Sci. USA* 81, 848

(1984)). Dnak protein interacts with lambda phage 0 and P proteins during phage replication (J. H. LeBowitz, C. Zylicz, C. Georgopoulos, R. McMacken, *Proc. Natl. Acad. Sci. USA* 82, 3988 (1985); and Dodson et al., *Proc. Natl. Acad. Sci. USA* 82, 4678 (1985)), again implicating hsp70 in the disruption of a tight protein-protein interaction. Like clathrin uncoating, this is an example of a specific function that exploits the general properties of the hsp70-like proteins.

In cells that overproduce the transformation-associated protein p53, stable complexes form between p53 and hsp70-related proteins (O. Pinhasi-Kimhi, D. Michalovitz, A. Ben-Zeev, M. Oren, *Nature* 320, 182 (1986)). Mutations in the gene encoding p53 that inactivate its tumor suppressing potential also result in the synthesis of mutant proteins which show preferential association with hsp70-like proteins and have an increased half-life (C. A. Findley, et al., *Mol. Cell. Biol.* 8, 531 (1988)). It is hypothesized that this interaction leads to a higher stability of p53, and the complex can be dissociated in vitro with ATP. Interestingly, p53 synthesized in *E. coli* is found in association with dnak protein (C. F. Clarke, et al., *Mol. Cell. Biol.* 8, 1206 (1988)).

Several eukaryotic cell DNA viruses, i.e., adenovirus (J. R. Nevins, *Cell* 29, 913 (1982)), herpes Virus (E. L. Notarianni, C. M. Preston, *Virology* 123, 113 (1982)), and Simian Virus 40 and polyoma viruses (E. W. Khanjian, H. Turler, *Mol. Cell. Biol.* 3, 1 (1983)) activate synthesis of hsp70 early in infection. Newcastle Disease Virus, an RNA virus, induces hsp70 and hsp90 in infected chicken cells (P. C. Collins, L. E. Hightower, *J. Virol.* 44, 703 (1982)). Hsp70 itself is reported to have a protease activity (H. K. Mitchell, N. S. Petersen, C. H. Buzin, *Proc. Natl. Acad. Sci. USA* 82 4969 (1985)).

Two proteins related to hsp70 and hsp90 and regulated by glucose starvation have been identified as grp78 and grp94, respectively (A. S. Lee, J. Bell, J. Ting, *J. Biol. Chem.* 259, 4616 (1984); and R. P. C. Shiu, J. Pouyssegur, I. Pastan, *Proc. Natl. Acad. Sci. USA* 74, 3840 (1977)). Grp's are not normally heat-inducible, but are overproduced under a variety of other physiological stresses such as anoxia, paramyxovirus infection, and treatment of cells with glycosylation inhibitors (S. C. Chang, et al., *Proc. Natl. Acad. Sci. USA* 84, 680 (1987)) or the calcium ionophore A23187 (Lin et al., *Mol. Cell Biol.* 6, 1235 (1986)). These proteins are abundant in secretory cells and are found associated with endoplasmic reticulum, and may possibly carry out the same functions as hsp's.

Grp78 is about 60% homologous to hsp70 and is identical to BiP (S. Munro, H. Pelham, *Cell* 46, 291 (1986)), a protein known to bind to the immunoglobulin heavy chains in pre-B cells that do not make light chains (Bole et al., *J. Cell Biol.* 102, 1558 (1986)). This finding suggests that grp78 prevents the formation of heavy chain aggregate and thus helps the process of immunoglobulin assembly. Grp78 binds to the aberrant proteins to keep them soluble in the same way as hsp70 acts on heat-denatured nuclear proteins. For example, it associates with mutants of hemagglutinin of influenza virus that fail to assemble into a mature trimeric glycoprotein (M. J. Gething, K. McCammon, J. Sambrook, *Cell* 46, 939 (1986)). Mammalian cell lines with decreased amounts of grp78 show increased secretion of mutant proteins (A. Dorner, M. Krane, R. Kaufman, *J. Cell Biochem. Suppl.* 12D, 276 (1988)).

Grp94 has been partially sequenced, showing that the protein is more than 50% homologous to yeast hsp90 and Drosophila hsp83 (P. K. Sorger, H.R.B. Pelham, *J. Mol. Biol.* 194, 341 (1987)). It is glycosylated, soluble in the absence of detergents, and is probably a luminal protein. The role of grp94 is even less understood than that of grp78.

There is also little information on the function of the low molecular weight hsp's. A stretch of 75 amino acids which are conserved among four small Drosophila hsp's is found to be 50% homologous to the B chain of mammalian lens alpha crystallins (H. Bloemendal, T. Berns, A. Zweers, H. Hoenders, E. L. Benedetti, *Eur. J. Biochem.* 24, 401 (1972); and T. D. Ingolia, E. A. Craig, *Proc. Natl. Acad. Sci. USA* 79, 2360 (1982)), suggesting that these hsp's may serve some kind of structural role. The Drosophila hsp's form large insoluble aggregates in a perinuclear region of the cell after prolonged heat shock (N. C. Collier, M. J. Schlesinger, *J. Cell Biol.*, 103, 1495 (1986); and L. Nover, K.-D. Scharf, D. Neumann, *Mol. Cell. Biol.* 3, 1648 (1983)), but these aggregates dissociate during cell recovery.

There is also an association of srp's with acquired drug resistance. Exposure of renal adenocarcinoma cells to heat shock or chemical stresses has shown that the major MDR1 gene promoter has heat shock elements and its expression (both mRNA and protein) is increased by these stresses, with a concomitant development of resistance to vinblastine (K.-V. Chin, S. Tanaka, G. Darlington, I. Pastan, M. M. Gottesman, *J. Biol. Chem.* 265, 221 (1990)). MDR1 RNA levels, however, did not change following stresses that normally induce grp's. Similarly, in Chinese hamster ovary cells, Shen et al. (J. Shen, et al., *Proc. Natl. Acad. Sci. USA* 84, 3278 (1987)) found that the induction of grp's did not change the level of MDR1-encoded P-glycoprotein. But these cells nevertheless acquired resistance to doxorubicin through an unknown mechanism. These observations suggest that some srp's may also be involved either indirectly or directly in conferring drug resistance to cells. In renal cells, MDR1-encoded P-glycoprotein may additionally protect cells from the effects of heat shock and chemical stresses.

More recently, Huot et al. (personal communication) found that transfection of Chinese hamster ovary cells with the hsp27 gene results in development of multidrug resistance. These studies indicate the role of a specific hsp in the phenomenon of multidrug resistance.

Prognosis in clinical cancer is an area of great concern and interest. It is important to know the aggressiveness of the malignant cells and the likelihood of tumor recurrence in order to plan the most effective therapy. Breast cancer, for example, is managed by several alternative strategies. In some cases local-regional and systemic radiation therapy is utilized while in other cases mastectomy and chemotherapy or mastectomy and radiation therapy are employed. Current treatment decisions for individual breast cancer patients are frequently based on (1) the number of axillary lymph nodes involved with disease, (2) estrogen receptor and progesterone receptor status, (3) the size of the primary tumor, and (4) stage of disease at diagnosis (G. M. Clark et al., *N. Engl. J. Med.* 309. 1343 (1983)). It has also been reported that DNA aneuploidy and proliferative rate (percent S-phase) can help in predicting the course of disease (L. G. Dressler et al., *Cancer* 61, 420 (1988); and G. M. Clark et al., *N. Engl. J. Med.* 320, 627 (1989)). However, even with these additional factors, we are still unable to accurately predict the course of disease for all breast cancer patients. There is clearly a need to identify new markers, in order to separate patients with good prognosis who will need no further therapy from those more likely to recur who might benefit from more intensive treatments.

This is particularly true in the case of breast cancer which has not progressed to the axillary lymph nodes. There is now evidence in prospective randomized clinical trials that adjuvant endocrine therapy and adjuvant chemotherapy beginning immediately after surgical removal of the primary breast tumor can be of benefit in some of these node-negative patients. This has led to official and unofficial recommendations that most if not all node-negative breast cancer patients should be considered for some form of adjuvant therapy. But since the majority (~70%) of these patients enjoy long-term survival following surgery and/or radiotherapy without further treatment, it may be inappropriate to recommend adjuvant therapy for all of these patients. If there were sufficiently good methods to distinguish those node-negative patients who are "cured" from those destined to recur, only the latter should be treated. Thus, there is a great need for a general method of predicting tumor recurrence in these patients and in cancer patients in general once the primary tumor is detected.

The present invention is a significant step in the ability to predict with some confidence the likelihood of cancer recurrence. It is clear from the extensive studies on the stress response proteins that they have an important physiological role, but until now no one has been able to relate their levels or presence to clinical manifestations of dysfunction. Now the survival risk to cancer patients can be better assessed and aggressive therapies applied as indicated to those in high risk groups.

The present invention is the discovery that the number and level of stress response proteins in primary tumor tissue show an unexpected and surprising correlation with tumor recurrence. Consequently, the present work represents a significant advancement in cancer management because early identification of patients at risk for tumor recurrence will permit aggressive early treatment with significantly enhanced potential for survival.

SUMMARY OF THE INVENTION

The present invention relates to a novel method for determining the likelihood of tumor recurrence and survival in cancer patients by utilizing a previously unrecognized relationship between stress response proteins and high probability of tumor recurrence. The relationship depends on the number and the levels of the stress response proteins.

It should be recognized that stress response proteins (srp's) are a class of proteins of which the previously recognized heat shock proteins (hsp's) are a subclass, and the glucose response (or glucose regulated) proteins (grp's) are another subclass. Since the hsp's respond to many stresses besides heat, there is a trend toward using the generic designation srp's for these proteins. In the present invention, srp's will refer to the class, while specific proteins will be given their original designations (e.g. hsp27).

The stress response proteins identified with this invention are heat shock proteins 27, 70 and 90 and glucose response protein 94. These are known in the art as members of families of proteins having molecular weights in humans in the range of 27, 70, 90 and 94 kDa respectively. It is intended that stress response proteins refer to any stress response protein produced in the tumor cell for which it would be possible, using the method of the present invention, to determine "overproduction" levels. As yet undiscovered or untested stress response proteins would also be expected to be correlated with tumor recurrence since they are produced in response to the same stresses that result in hsp27, 70, 90 and/or grp94 overproduction. Up to four stress response proteins have been associated with tumor recurrence, but since correlation increases with the number of stress response proteins, it is expected that detection of additional stress response proteins will further improve correlation.

In an embodiment of the invention, the presence of two or more of these proteins can be correlated with tumor recurrence. The level of any stress response protein utilized in this invention would first be determined to exceed a "basal" level by comparison with stress response proteins produced by a standard breast tumor cell line on deposit with the American Type Culture Collection (ATCC).

An important aspect of this invention is the association of "overproduction" levels of stress response proteins with tumor recurrence. Each protein must exceed a basal level before it is a significant factor in tumor recurrence. When basal levels are exceeded, the stress response is "overproduced" and indicates increased risk of tumor recurrence. On the other hand, the mere presence of one or more stress response proteins is not correlated with higher risk of tumor recurrence.

Overproduction is related to a level of srp's above a determined low or basal level and is different for each srp. Thus, in this invention a level of each protein was identified as a "cutoff" value, above which there was a significant correlation between the presence of the srp and tumor recurrence. Some "cutoff" values were not sharp in that clinical correlations were still significant over a range of values on either side of the cutoff; however, it was possible to select an optimal cutoff value for each stress response protein The cutoff value used for a given application is termed the "cutpoint".

The levels of grp94 and three hsp's (hsp90, hsp70, and hsp27) in a large cohort of well characterized human primary breast tumors with extensive clinical followup were measured. Results showed that overproduction of these proteins occurs relatively frequently in breast cancer, with considerable correlation among the four srp's. Furthermore, higher levels of all (grp94 marginally) were associated with tumor recurrence behavior in breast cancer patients having no tumor extensions to the axillary lymph nodes at primary treatment. Simultaneous occurrence of more than one srp was a more powerful predictor of poor disease-free survival; the higher the number of overproduced srp's, the greater was the risk of tumor recurrence. Relating these srp's to other clinical characteristics in breast cancer, associations with factors suggesting tumor invasiveness, hormone sensitivity, and poor cellular differentiation within the tumor were found.

A relative measure of "overproduction" is used in this invention. The units defining "overproduction" are relative to an arbitrarily assigned cancer cell line standard. In a preferred embodiment, MCF-7 human breast cancer cells (ATCC-HTB22 MCF-7) are grown under defined conditions. Aliquots of homogenized cells are analyzed along with each set of samples of test tissue by standard procedures. Each μg protein aliquot of MCF-7 cells is arbitrarily assigned a "one unit" value so that the level of any given stress response protein in the test sample is measured in units against this standard MCF-7 cell unit. Absolute values of the arbitrary "units" can be readily determined by one skilled in the art. It should be appreciated that the "overproduction" values selected are illustrative and that correlations may still exist between levels of stress response proteins falling somewhat below the given cutoff values and tumor recurrence. Selection of the cutoff values is determined by statistical considerations and does not imply an absolute value.

Correlations were determined by well known multivariate analysis techniques. Different statistical treatment can be used to define other sets of values for the stress response proteins which could improve correlations. For example, if improved correlations were found, overproduction values would differ somewhat from the cutoff values defined in the present invention. In the present invention, ranges of values were determined for each stress response protein In a preferred embodiment, optimal cutoff levels of the stress response proteins hsp27, 70, and 90 and grp94 were 126, 217, 32, and 45 units per 100 μg tumor protein. Above these levels, the proteins were considered overproduced and hence indicative of significant risk of tumor recurrence.

The stress response proteins useful in the practice of this invention are typically produced in response to cell stress. The four used in the present invention are the best known, but others have been discovered and are contemplated as being included in the invention. It is likely, for example, that grp78, another glucose response protein, will exhibit correlation with tumor recurrence when overproduced in cancer tissue. The details of measurement and correlation of grp78 would be analogous to those used in the present invention to determine overproduction of grp94 and hsp's 27, 70 and 90.

Diagnostic kits for determining the number and levels of stress response proteins in tissue samples are contemplated which are immunologically based. All kits would comprise a stress response protein standard, antibodies (preferably monoclonal) to each stress response protein, a negative control breast tumor extract, and a positive control breast tumor extract, and in a preferred embodiment would be provided in lyophilized form.

Several variations of kits based on antibody binding are envisioned. For example, use of a second antibody specifically directed against the first antibody in a sandwich type detection system can be used in well-known variations of the ELISA technique. Detection of second antibodies tagged with various labels, including radioisotopes, chromophores, enzymes, and the like could also be used. Another variation is the binding of an antibody, for example a monoclonal antibody, by a second biotinylated antibody followed by reaction with an avidin biotinylated horseradish peroxidase complex. If the first antibody is attached to a substrate such as an agarose bead or a microtiter plate well, the color developed can be quantitated relative to a standard supplied in the kit.

Although the applications of the invention which are described here are based on antibodies specific for each srp, it will be understood by those in the art that the level of each srp is related to the level of the messenger RNA (mRNA) which encodes it. Therefore, provided that the amino acid sequence of the srp is known, methods can easily be envisioned by which srp overproduction in tumors would be determined by measuring levels of the corresponding mRNA's. Rather than antibodies, complementary DNA's for each srp mRNA would be the specific recognition elements, and the existing techniques known as Northern blots, slot blots, in situ hybridizations, and polymerase chain reactions (PCR) would be applied. Messenger RNA levels have been used to determine production of corresponding proteins ( G. Bevilacqua, M. E. Sobel, L. A. Liotta and T. S. Steeg, Cancer Res. 49, 5185-5190 (1989)).

BRIEF DESCRIPTION OF THE DRAWINGS

FIG. 4 illustrates Kaplan-Meier recurrence curves for node-negative breast cancer patients based on higher levels of one or more of the stress response proteins.

DESCRIPTION OF PREFERRED EMBODIMENTS

Figure 1:
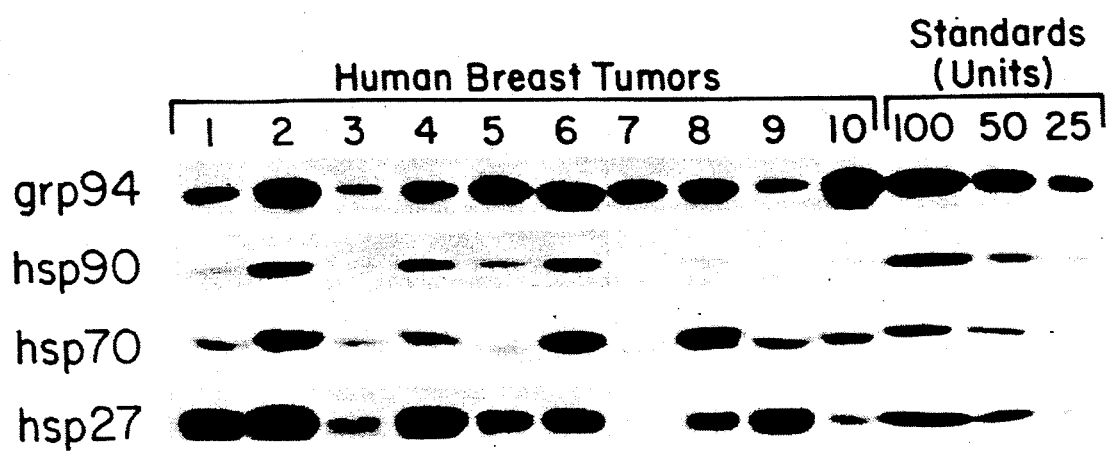
FIG. 1 shows a Western Blot analysis of ten human breast tumor extracts using monoclonal antibodies to hsp27, hsp70, hsp90, and grp94. An internal reference standard of an MCF-7 human breast cancer cell protein extract is shown as the standard against which relative units were calculated.
Figures 2A, 2B:
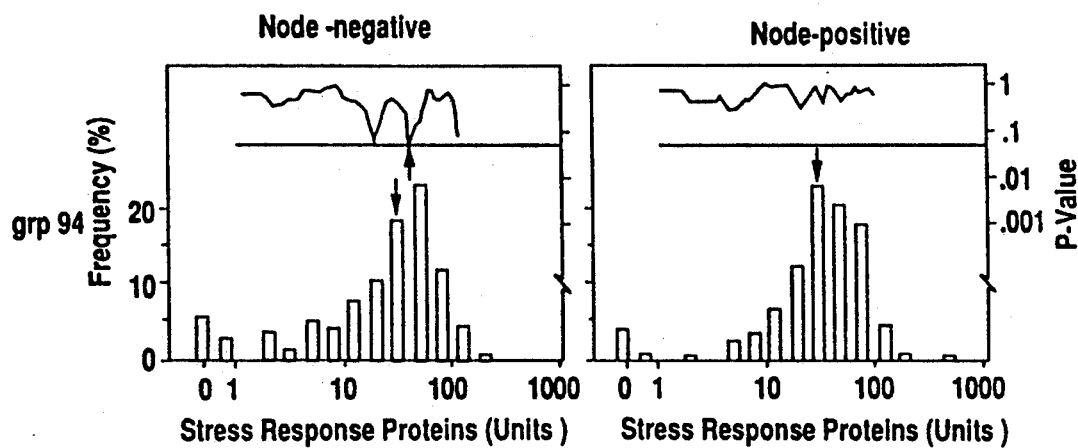
FIGS. 2A-2H are a series of graphs showing distributions of stress response proteins in node-negative and node-positive breast cancer patients, and the statistical significance of the full range of possible cutoff values for each srp in predicting recurrence.
Figures 2C, 2D:
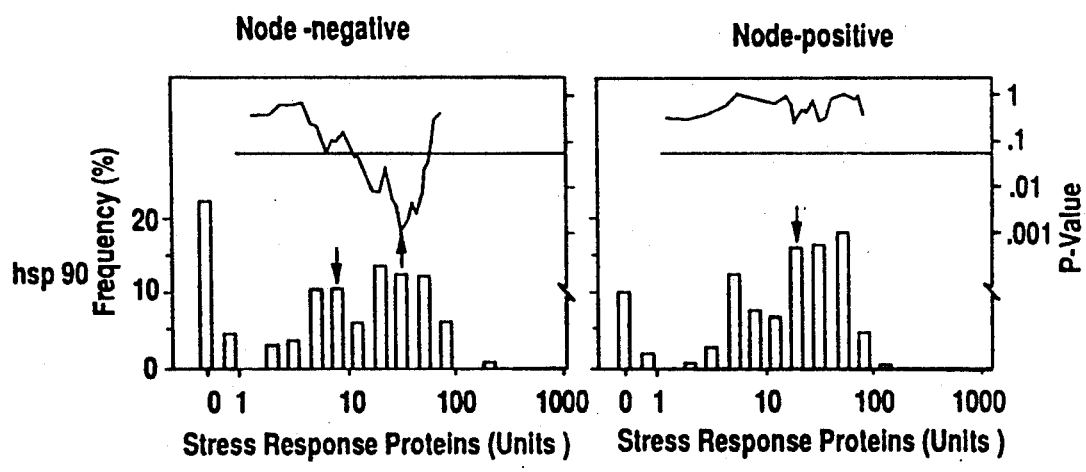
Figures 2E, 2F:
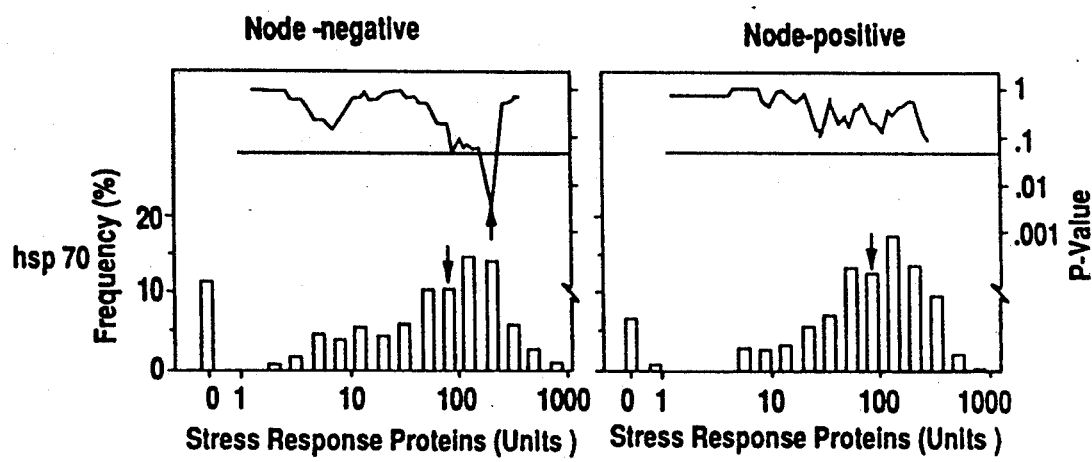
Figures 2G, 2H:
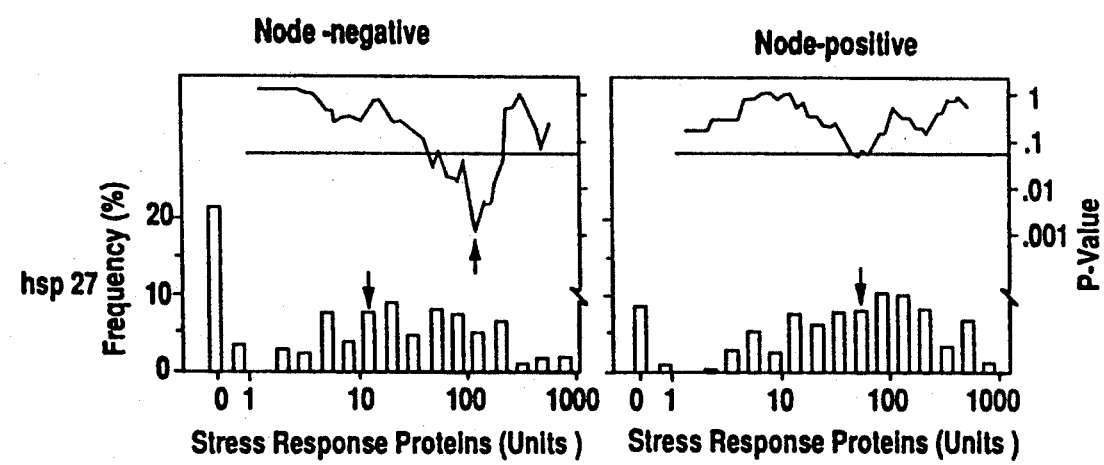
Figure 3B:
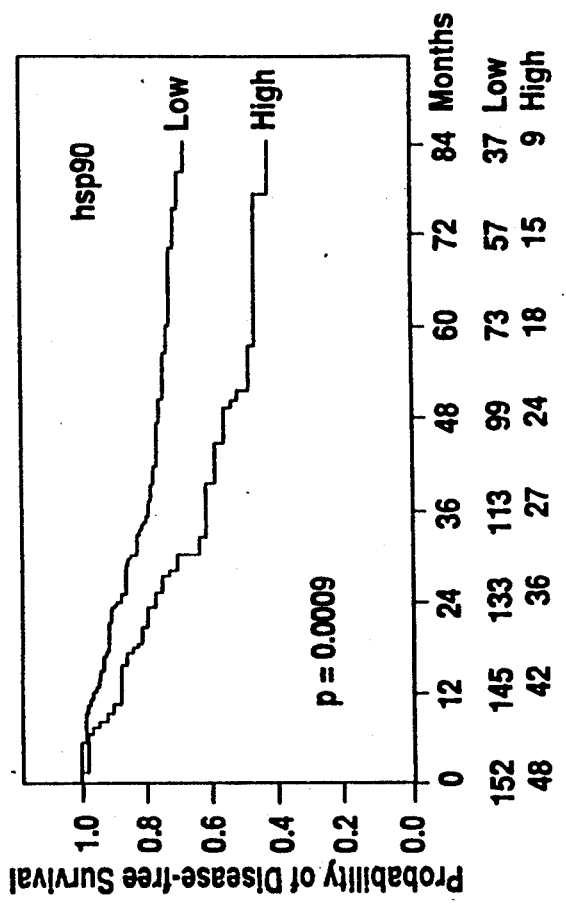
FIGS. 3A-3D show the association of stress response proteins with tumor recurrence for node-negative breast cancer patients using a Kaplan-Meier analysis of time to recurrence.
Figure 3A:
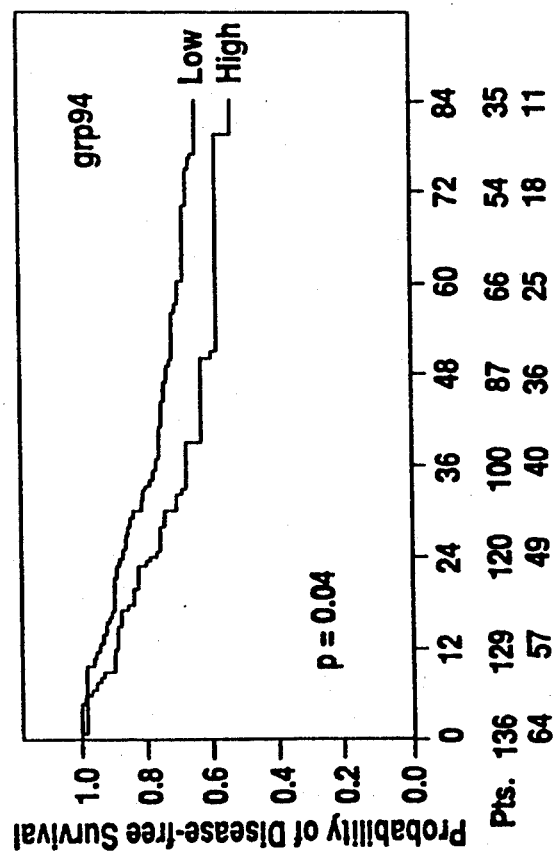
Figure 3D:
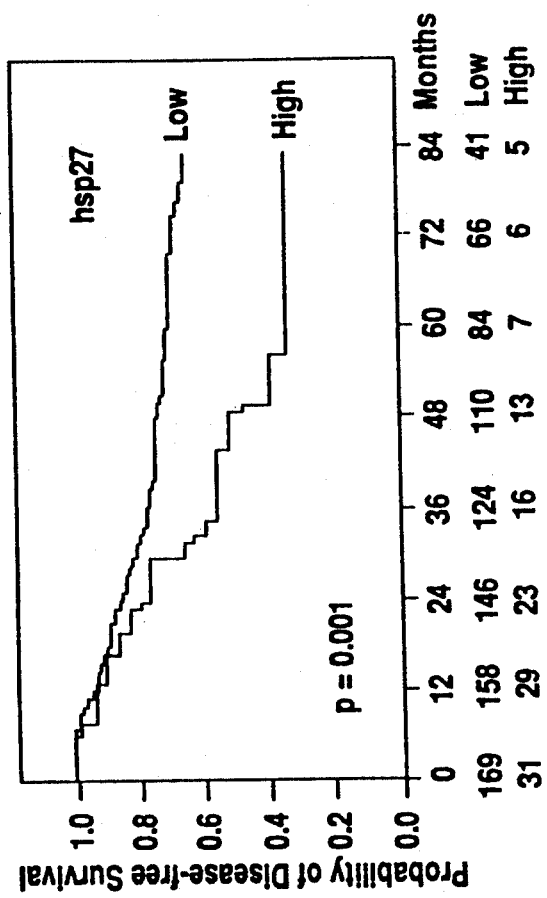
Figure 3C:
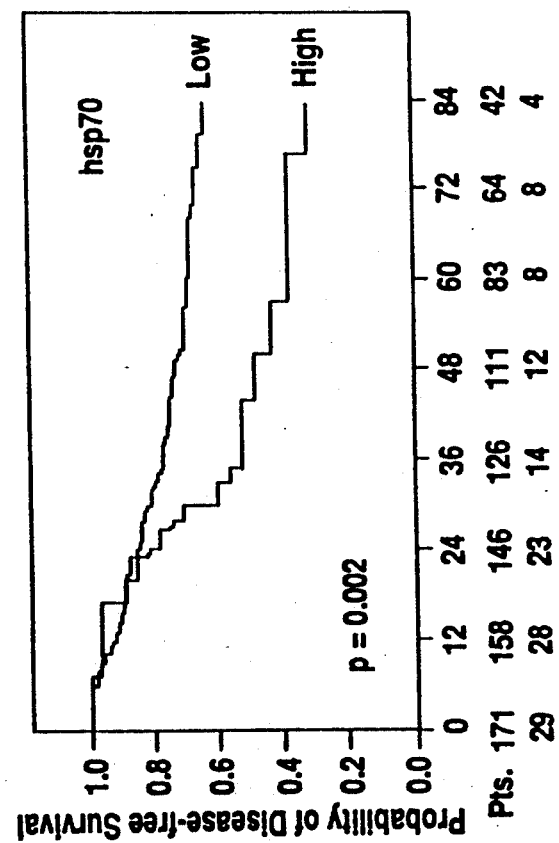

The method for predicting survival in cancer patients is based on an analysis of a cancerous tissue sample. Frozen, stored tumor tissues from 398 primary breast cancers were analyzed for the four srp's by a semi-quantitative Western Blot procedure in a blinded fashion, i.e. without prior knowledge of any tumor characteristics or disease outcome. Tissues for the quantitation of these proteins were obtained from the biopsy specimens. Values for estrogen receptor (ER), progesterone receptor (PgR), HER-2/neu oncogene protein (a growth factor receptor-like transmembrane glycoprotein of 185 kDa) ( A. K. Tandon, G. M. Clark, G. C. Chamness, A. Ullrich, W. L. McGuire, *J. Clin. Oncol.* 7, 1120 (1989)), DNA ploidy (a measure of DNA content) (L. G. Dressler, L. C. Seamer, M. A. Owens, G. M. Clark, W. L. McGuire, *Cancer* 61, 420 (1988)), and the 34 kDa mature form of cathepsin D (an estrogen-induced lysosomal acidic protease) (A. K. Tandon, G. M. Clark, G. C. Chamness, J. M. Chirgwin, W. L. McGuire, *N. Engl. J. Med.* 322, 297 (1990)) were available on the tumor specimens analyzed. To account for the variability in content of tumor cells in different regions within the same specimen, in the first step breast tumors were mechanically pulverized in liquid nitrogen to obtain a uniform distribution of tumor cells. To further minimize the potential risk of uneven dilution of tumor cell proteins with stromal proteins, larger quantities (100 mg) than needed (10 mg) were used for protein extraction. Total proteins were extracted with sodium dodecyl sulfate (A. K. Tandon, G. M. Clark, G. C. Chamness, A. Ullrich, W. L. McGuire, *J. Clin. Oncol.* 7, 1120 (1989)). One hundred micrograms of extracted proteins were subjected to Western Blot analysis using monoclonal antibodies to grp94 (D. P. Edwards, N. L. Weigel, W. T. Schrader, B. W. O'Malley, W. L. McGuire, *Biochem.* 23, 4427 (1984); and D. R. Sargan, M.-J. Tsai, B. W. O'Malley, *Biochem.* 25, 6252 (1986); the monoclonal antibody 9G10 used here reacts with purified grp94 in Western Blot assay, unpublished observation from W. J. Welch's laboratory), hsp90 (S. Schuh et al., *J. Biol. Chem.* 260, 14292 (1985)), hsp70 (a gift from W. J. Welch), and hsp27 (D. J. Adams, H. Hajj, D. P. Edwards, R. J. Bjercke, W. L. McGuire, *Cancer Res.* 43, 4297 (1983)). Remaining tumor protein extracts were immediately frozen and stored at −70° C. Examples of ten tumors along with an internal reference standard of MCF-7 human breast cancer cells (see below) are shown in FIG. 1. The levels of these srp's in individual tumors were calculated in relative units per one hundred micrograms tumor protein by the ratio of the integrated signal in the tumors relative to the MCF-7 internal standard.

The stress response proteins in tumors were measured against the content of the same stress response proteins in a cell culture of human breast cancer cells. These cells were originally obtained from the Michigan Cancer Foundation, and can be purchased from the American Type Culture Collection (ATCC HTB22 MCF-7). In preferred practice the cells are cultured in Eagle's minimum essential medium supplemented with nonessential amino acids, gentamycin, calf serum, L-glutamine and bovine insulin at near physiological pH, as specified in Example 5.

A second step was to compare the levels of each srp with cancer recurrence. Levels of all four srp's ranged from undetectable to high. Actual ranges per 100 µg tumor proteins were 0–557 units for grp94; 0–173 units for hsp90; 0–862 units for hsp70; and 0–2645 units for hsp27. Distributions of the four srp's under study for node-negative and node-positive breast cancer patients are shown in FIG. 2. The distributions for these srp's in both groups were approximately log-normal. Median values of srp's in node-positive versus node-negative breast tumors were as follows: 37 vs 32 for grp94 (P =0.2); 20 vs 10 for hsp90 (P=0.001); 82 vs 66 for hsp70 (P =0.08); and 48 vs 4 for hsp27 (P<0.0001).

Correlations of the srp's with clinical manifestations of breast cancer disease and its ultimate outcome were determined. Conventionally, the median value of a given parameter is used to distinguish patients with high levels of the parameter from those with low levels. However, median values of all four srp's failed to discriminate these patients into low and high risks of disease recurrence. Therefore, a biologically meaningful cutoff value was sought for different srp's to distinguish patients at high risk of relapse. A wide range of cutoff values gave statistically significant separation of disease-free survival probabilities in the group of 200 node-negative patients (74 months median followup for patients still alive) for hsp90 (12 to 59 units), hsp70 (120 to 250 units), and hsp27 (46 to 232 units) (FIG. 2). For grp94, unlike hsp's, there was only one single cutpoint at 45 units. The optimum cutpoints for hsp90, hsp70, and hsp27 were 32, 217, and 126 units, respectively. For 198 node-positive patients the median followup was 61 months for patients still alive; however, in contrast to node-negative patients, no cutpoints gave a significant segregation of low and high risk patients for tumor recurrence (hsp27 marginally reached statistical significance but the apparent cutpoint range was extremely limited, FIG. 2).

The interrelationship of four srp's in node-negative breast tumors was determined. Tumors were classified as low or high using the optimum cutpoint for each srp. About fifty percent (101/200) of the tumors were found to contain low levels of all four srp's, leaving 50% as high for either one, two, three, or all four srp's. Only 2.5% (5/200) of tumors contained high levels of all four srp's. Therefore, though these four srp's were significantly correlated to each other, all were not concomitantly overproduced in all tumors, perhaps reflecting the diverse nature of physiological stress from tumor to tumor. Using the optimum cutpoints, 33.5% of tumors were high for grp94; 24% for hsp90; 15% for hsp70; and 15.5% for hsp27; either alone or in various combinations with the other three srp's. Data on overlapping incidence of srp's are shown in Table 1, and the correlation values are given in Table 2. A higher incidence of high levels of hsp90 and grp94 indicates that these srp's may be more sensitive indicators of the biological stress.

TABLE 1

Interrelationship of Four Stress Response Proteins with Each Other

| % Positive for: | Which are also Positive for: | | | |
|---|---|---|---|---|
| | grp94 | hsp90 | hsp70 | hsp27 |
| grp94 | 100 | 50 | 16 | 17 |
| hsp90 | 67 | 100 | 29 | 35 |
| hsp70 | 34 | 48 | 100 | 55 |
| hsp27 | 35 | 55 | 52 | 100 |

All pairwise comparisons were statistically significant ($P < 0.05$).

Spearman rank correlation coefficients (r) among these four srp's were all statistically significant ($P<0.05$) and varied from 0.32 to 0.67 (see Table 2).

TABLE 2

Spearman Rank Correlation Coefficients (r) for the Pairwise Interrelationship of Four Stress Response Proteins With Each Other

| | grp94 | hsp90 | hsp70 | hsp27 |
|---|---|---|---|---|
| grp94 | | | | |
| hsp90 | 0.67 | | | |
| hsp70 | 0.44 | 0.61 | | |
| hsp27 | 0.32 | 0.50 | 0.63 | |

All pairwise comparisons were statistically significant ($P < 0.05$).

Association of srp's with other tumor characteristics which are biological indicators of metastatic potential, hormone responsiveness, or relative histopathologic differentition was investigated. Data are summarized in Tables 3A and 3B. All four srp's were directly associated with high levels of cathepsin D, an estrogen-induced lysosomal protease supposed to be a marker of metastatic potential (hsp27 failed to reach statistical significance). Similar results were found using cathepsin D directly as a clinical discriminator in these sets of node-negative and node-positive patients (A. K. Tandon, G. M. Clark, G. C. Chamness, J. M. Chirgwin, W. L. McGuire, *N. Engl. J. Med.* 322, 297 (1990)).

In addition to cathepsin D, the following correlations/associations were observed: hsp27 and hsp70 with estrogen and progesterone receptor status; hsp90 and grp94 with aneuploidy; hsp70, hsp90, and grp94 with nuclear grade; and hsp27 and hsp90 with HER-2/neu oncogene protein. No significant correlations were found with tumor size or patient age.

The data in Tables 3A and 3B were obtained by analysis of tumors from 398 breast cancer patients ranging in age from 26 to 82 years with a median of 58 years.

Tumor grp94≧45 units; hsp90≧32 units; hsp70≧217 units; and hsp27≧126 units per 100 μg of total tumor proteins were categorized as high (positive). Nodal status was considered negative when no lymph nodes contained tumor cells and positive if one or more nodes showed the presence of malignant cells. Tumor size (largest diameter) was recorded at the time of surgery. Levels of estrogen receptor (ER) and progesterone receptor (PgR) in fresh tumor cytosols were determined by standard methods (W. L. McGuire, M. De La Garza, G. C. Chamness, Cancer Res. 37, 637 (1977); B. Powell, R. E. Garola, G. C. Chamness, W. L. McGuire, ibid, 39, 1678 (1979)) and are expressed as fmoles per mg cytosolic proteins. Ploidy (DNA content) was determined by flow cytometric analysis (L. G. Dressler, L. C. Seamer, M. A. Owens, G. M. Clark, W. L. McGuire, Cancer 61, 420 (1988)). Levels of the HER-2/neu oncogene protein and the 34 kDa mature form of cathepsin D were quantitated by Western blotting and densitometry methods (A. K. Tandon, G. M. Clark, G. C. Chamness, A. Ullrich, W. L. McGuire, J. Clin. Oncol. 7, 1120 (1989); A. K. Tandon, G. M. Clark, G. C. Chamness, J. M. Chirgwin, W. L. McGuire, N. Engl. J. Med. 322, 297 (1990)). Analysis of data for association between srp's and other characteristics in breast cancer was performed using two-way contingency tables and nonparametric correlation coefficients.

TABLE 3A

Relationship Between Stress Response Proteins and Other Clinical Characteristics in Node-Negative Breast Cancer

| Characteristic | n | grp94 % grp+ | P | hsp90 % hsp+ | P | hsp70 % hsp+ | P | hsp27 % hsp+ | P |
|---|---|---|---|---|---|---|---|---|---|
| Cathepsin D | | | | | | | | | |
| <75 units | 136 | 24 | 0.0006 | 17 | 0.0006 | 9 | 0.009 | 13 | 0.09 |
| ≧75 units | 64 | 48 | | 39 | | 27 | | 22 | |
| Nuclear Grade | | | | | | | | | |
| 1 | 6 | 33 | | 0 | | 0 | | 0 | |
| 2 | 103 | 28 | 0.06 | 18 | 0.002 | 12 | 0.08 | 14 | 0.21 |
| 3 | 70 | 46 | | 40 | | 23 | | 21 | |
| Histologic Grade | | | | | | | | | |
| 1 | 6 | 33 | | 0 | | 0 | | 0 | |
| 2 | 111 | 30 | 0.12 | 24 | 0.17 | 14 | 0.39 | 17 | 0.54 |
| 3 | 62 | 45 | | 32 | | 19 | | 16 | |
| Estrogen Receptor | | | | | | | | | |
| ≧3 fmol/mg | 142 | 30 | 0.25 | 26 | 0.29 | 18 | 0.02 | 18 | 0.09 |
| <3 fmol/mg | 58 | 38 | | 19 | | 5 | | 9 | |
| Progesterone Receptor | | | | | | | | | |
| ≧5 fmol/mg | 99 | 27 | 0.16 | 23 | 0.80 | 24 | 0.0001 | 20 | 0.07 |
| <5 fmol/mg | 101 | 37 | | 25 | | 5 | | 11 | |
| Tumor Size | | | | | | | | | |
| ≧2 cm | 73 | 30 | 0.67 | 21 | 0.39 | 18 | 0.31 | 12 | 0.35 |
| >2 cm | 127 | 33 | | 26 | | 13 | | 17 | |
| Ploidy | | | | | | | | | |
| Diploid | 72 | 24 | 0.03 | 14 | 0.008 | 10 | 0.12 | 13 | 0.31 |
| Aneuploid | 116 | 39 | | 31 | | 18 | | 18 | |
| Age | | | | | | | | | |
| ≧50 years | 137 | 33 | 0.71 | 27 | 0.14 | 18 | 0.07 | 15 | 0.92 |
| <50 years | 63 | 30 | | 17 | | 8 | | 16 | |
| HER-2/neu | | | | | | | | | |
| <100 units | 171 | 32 | 0.66 | 21 | 0.01 | 16 | 0.23 | 13 | 0.04 |
| ≧100 units | 28 | 36 | | 43 | | 7 | | 29 | |

TABLE 3B

Relationship Between Stress Response Proteins and Other Clinical Characteristics in Node-Positive Breast Cancer

| Characteristic | n | grp94 % grp+ | P | hsp90 % hsp+ | P | hsp70 % hsp+ | P | hsp27 % hsp+ | P |
|---|---|---|---|---|---|---|---|---|---|
| Cathepsin D | | | | | | | | | |
| <75 units | 101 | 64 | 0.001 | 30 | 0.19 | 15 | 0.51 | 22 | 0.08 |
| ≧75 units | 98 | 85 | | 39 | | 18 | | 33 | |
| Estrogen Receptor | | | | | | | | | |
| ≧3 fmol/mg | 142 | 75 | 0.89 | 35 | 0.94 | 21 | 0.007 | 35 | 0.0002 |
| <3 fmol/mg | 57 | 74 | | 34 | | 5 | | 9 | |
| Progesterone Receptor | | | | | | | | | |
| ≧5 fmol/mg | 100 | 76 | | 34 | | 24 | | 36 | |

TABLE 3B-continued

Relationship Between Stress Response Proteins and Other Clinical Characteristics in Node-Positive Breast Cancer

| Characteristic | n | grp94 % grp+ | P | hsp90 % hsp+ | P | hsp70 % hsp+ | P | hsp27 % hsp+ | P |
|---|---|---|---|---|---|---|---|---|---|
| <5 fmol/mg | 99 | 73 | 0.60 | 35 | 0.92 | 9 | 0.005 | 18 | 0.005 |
| Tumor Size | | | | | | | | | |
| <2 cm | 34 | 76 | 0.76 | 26 | 0.29 | 12 | 0.41 | 32 | 0.45 |
| ≧2 cm | 165 | 74 | | 36 | | 18 | | 26 | |
| Age | | | | | | | | | |
| ≧50 years | 129 | 74 | 0.98 | 37 | 0.34 | 21 | 0.03 | 30 | 0.18 |
| <50 years | 70 | 74 | | 30 | | 9 | | 21 | |
| HER-2/neu | | | | | | | | | |
| <100 units | 163 | 36 | 0.21 | 32 | 0.10 | 18 | 0.07 | 30 | 0.07 |
| ≧100 units | 34 | 50 | | 47 | | 6 | | 15 | |
| No. of Positive Nodes | | | | | | | | | |
| 1-3 | 74 | 39 | 0.82 | 38 | 0.42 | 14 | 0.37 | 28 | 0.76 |
| >3 | 125 | 38 | | 32 | | 18 | | 26 | |

The association of each srp with the likelihood of development of recurrent breast cancer was studied. Kaplan-Meier analyses of time to recurrence for the node-negative patients are shown in FIG. 3. Patients with higher levels of grp94, hsp90, hsp70, or hsp27 in primary tumors were at a greater risk of developing early recurrent cancer compared to those with lower levels of these proteins.

Both hsp27 and hsp70 distinguished patients with different recurrence rates within 18 months of surgical removal of tumor. Hsp90 separated the two groups of patients within a few months of primary treatment.

Kaplan-Meier recurrence curves were constructed based upon the higher levels of any one of the four, two of the four, three of the four, or all four srp's in the tumor, and compared with those containing only low levels of all four srp's (FIG. 4). Concomitant presence of more than one high srp in the tumor was highly indicative of early recurrence of disease. The five-year actuarial recurrence was 24% to 27% in patients with low levels of all four srp's or with high level of only one of the four srp's, 47% in patients with high levels of two of four srp's, and 78% to 80% in patients with high levels of three or all four srp's. Data are shown in Table 4.

TABLE 4

Five-Year Actuarial Recurrence of Node-Negative Breast Cancer Patients as a Function of Stress Response Proteins (srp's)

| No. of Positive srp's | No. of Patients | % Recurrence ± S.E. |
|---|---|---|
| None | 101 | 24 ± 4 |
| One of four | 48 | 27 ± 7 |
| Two of four | 34 | 47 ± 9 |
| Three of four | 12 | 78 ± 13 |
| All four | 5 | 80 ± 18 |

High levels of srp's, defined in Table 3A, are denoted as positive.

Stress response proteins and several other tumor characteristics were subjected to a multivariate analysis to explore their independent contribution in predicting disease-free survival probability in node-negative breast cancer patients. Ploidy, nuclear grade, and histologic grade were not included in this analysis since values for these variables were not available for many of the tumors.

A partially non-parametric regression model was used to evaluate the predictive power of various combinations and interactions of prognostic factors in a multivariate manner (N. E. Breslow, Int. Stat. Rev. 43, 45 (1975); D. R. Cox, J. R. Stat. Soc. B. 34, 187 (1972); J. D. Kalbfleisch and R. L. Prentice, The Statistical Analysis of Failure Time Data, New York, Wiley, 1980)). Variables were entered stepwise and the relative risks are presented only for the retained variables. Median clinical followup time for patients still living was 74 months with a range of 29 to 154 months.

Stress response (P=0.001) and cathepsin D (P=0.004) appeared as independent predictors of early recurrence, as indicated in Table 5. Relative risk for stress response was 1.4 per additional high srp. Inclusion of ploidy in multivariate analysis did not affect the dominance of srp's and cathepsin D. However, when patients with zero or one high srp were grouped and compared with all patients with two or more high srp's, the statistical significance of srp's was slightly weakened.

TABLE 5

Stress Response Proteins and Other Tumor Characteristics in Multivariate Disease-Free Survival in 199 Node-Negative Breast Cancer Patients

| Factor | Multivariate P-Value | Relative Risk |
|---|---|---|
| Stress Response Proteins | 0.001 | 1.4* |
| Cathepsin D | 0.004 | 2.1 |
| Patient Age | 0.08 | |
| Progesterone Receptor | 0.11 | |
| HER-2/neu Protein | 0.13 | |
| Estrogen Receptor | 0.61 | |
| Tumor Size | 0.91 | |

*srp's were considered as an ordinal variable (0 to 4+) so the relative risk is shown as per positive (i.e. high level) srp.

The four srp's analyzed are frequently present in primary breast tumors and are found to be associated with clinical variables suggesting lymph node invasion, tumor aggressiveness, hormone-responsiveness, and histopathologic de-differentiation. Breast cancer patients whose tumors contained lower levels of srp's had a significantly greater likelihood of surviving free of recurrence (second tumor) than patients with higher levels of srp's. Simultaneous occurrence of high levels of more than one srp is a stronger indicator of early disease-recurrence. In multivariate analysis, stress response joins cathepsin D in predicting early tumor metastasis.

Kits useful in the present invention comprise a carrier having compartments to receive several closed containers, the number depending on the specific reagents required for the method of analysis. All kits would provide a first container means comprising a stress response protein standard which contains known levels of hsp27, 70, 90 and grp 94; a second container means comprising a negative control breast tumor extract, a third container means comprising a positive control breast tumor extract, and a fourth container means comprising four monoclonal antibodies to the four stress response proteins Methods of stress response protein determination could be based on Western Blot, ELISA, or immunohistochemical analysis.

In a Western Blot procedure, a breast tumor sample is pulverized in liquid nitrogen to obtain a uniform distribution of cells, extracted, and total protein determined. After polyacrylamide gel electrophoresis and incubation with the appropriate antibodies, the sample srp bands are measured by densitometry and reported as a ratio against the srp bands of the included standards. The ratios are related to "cutoff" values as described earlier which indicate tumor recurrence risk.

An immunohistochemical method would be useful in kit form. The tumor sample is sectioned and fixed on an adhesive-coated slide which can be provided with the kit. Six sections are incubated with a normal animal serum, then four of these are treated with four different monoclonal antibodies to the stress response proteins and two with antibody negative controls. The antibodies are also applied to four control slides provided with the kit. All sections are incubated with biotinylated second antibody, incubated with avidin and biotinylated peroxidase, then incubated with diaminobenzidine and osmium tetroxide, and stained with methyl green. Positive staining shows brown coloration in the cytoplasm and is quantitated by determining both the fraction of stained tumor cells in several fields and the degree of their positivity to develop an H-score, as is presently done for a number of other proteins.

An ELISA assay kit would provide the monoclonal antibodies to the stress response proteins, the stress response protein standards, positive and negative breast tumor cytosol controls, and a second set of monoclonal antibodies to the stress response proteins coupled to horseradish peroxidase.

EXAMPLE 1 Detection and Measurement of Stress Response Proteins

Total proteins from tumor tissues or cell pellets were extracted with sodium dodecyl sulfate (SDS). Protein concentration in the SDS-extract was determined by the BCA method (P. K. Smith et al., Anal. Biochem. 150, 76 (1985)). SDS-extracted proteins were mixed with a sample buffer to achieve a final concentration of 135 mM Tris (pH 6.8), 2% SDS, 10% glycerol, 5% dithiothreitol, and 0.01% pyronin dye and the samples were heated in a boiling water bath for five minutes. Tumor proteins (100 μg) were resolved on 10% polyacrylamide vertical slab gels using 3% stacking gel. An SDS extract of MCF-7 human breast cancer cells was included at three concentrations (100 μg, 50 μg, and 25 μg protein, corresponding to 100, 50 and 25 arbitrary units of each stress response protein) in each gel as an internal reference standard. Transfer of separated proteins onto 0.2 μ nitroscreens (Dupont) was performed at 200 mAmp for 16 hours at 4° C. Following blocking of non-specific sites with 5% condensed milk powder (Carnation) for 1 hour, blots were incubated with culture supernatant of a hybridoma clone secreting rat monoclonal antibody (MAb) to grp94 (clone 9G10) overnight at 4° C. $^{125}$I-labeled sheep anti-rat IgG (100,000 cpm/ml; Amersham Corp) was used as the second antibody. After washing, the blots were exposed for 20-24 hours to X-OMAT X-ray film (Kodak) at −70° C. The same membranes were next reacted with purified mouse MAb to hsp70 (C92) at 1 μg/ml followed by $^{125}$I-labeled sheep anti-mouse IgG (100,000 cpm/ml; Amersham Corp) and exposed to X-ray film as described above, and then incubated with a mouse MAb to hsp27 (1 μg/ml) again followed by radiolabeled second antibody and x-ray film autoradiography. For measuring hsp90, another set of gels was run under the same conditions as described above and membranes were incubated with a mouse MAb (AC88, 1 μg/ml) followed by incubation with $^{125}$I-labeled anti-mouse IgG second antibody and exposure to X-ray film. The level of srp's in individual tumors was quantitated by densitometric scanning of the pertinent band on the autoradiogram in a Beckman DU-7 spectrophotometer, and expressed in relative units by comparison with the MCF-7 internal reference standard. The srp values in FIG. 1 for ten tumors (1 to 10) were: 33, 85, 19, 46, 70, 74, 54, 54, 27, 108 for grp94; 23, 76, 13, 50, 32, 58, 6, 16, 4, 12 for hsp90; 63, 261, 75, 119, 46, 211, 46, 211, 86, 86 for hsp70; and 194, 245, 41, 179, 91, 112, 5, 61, 139, 31 for hsp27.

EXAMPLE 2 Determination of Optimum Cutoff Values

Cutoff values for the four srp's that best distinguish patients at high risk for relapse were established by determining P-values for disease-free survival using each possible cutoff value. FIG. 2 graphically displays these P-values for both node-positive and node-negative breast cancer patients. A horizontal line is drawn at the P =0.05 level to show statistical significance. Upward arrows indicate the optimum cutpoints. Range and optimum cutoff values for the four srp's in node-negative breast cancer patients are given below:

| Range and Optimum Cutoff Values for srp's in Breast Tumors | | | |
|---|---|---|---|
| # | Stress Response | Cutoff Range | Optimum Cutpoint |
| 1. | grp94 | 45 units | 45 units |
| 2. | hsp90 | 12–59 units | 32 units |
| 3. | hsp70 | 120–250 units | 217 units |
| 4. | hsp27 | 45–232 units | 126 units |

EXAMPLE 3 Determination of Recurrence Relative to Stress Response Protein Level Based on optimum cutoff determinations, high srp's are defined as follows: grp94≧45 units, hsp90≧32 units, hsp70≧217 units, and hsp27≧126 units per 100 μg tumor proteins. Patients were followed for disease-free survival. Any post-surgical appearance of malignancy either near to or distant from the operated breast was considered as recurrence of disease. Survival curves were constructed and shown in FIG. 3 (E. L. Kaplan and P. Meier, J. Am. Stat. Assoc. 53, 457 (1958)) and the log rank test for censored survival data was used to test the statistical significance of difference between the curves (N. Mantel, *Cancer Chemother. Rep.* 50, 163 (1966)). All computations were done with the Biomedical Computer Programs—P series. The recurrence curves were based on a clinical followup period of 29 to 154 months, with a median of 74 months for patients still alive at the time of analysis. Values below the X-axis indicate the number of patients at risk at the interval shown.

EXAMPLE 4 Determination of Disease-Free Survival Relative to Number of High Level Stress Response Proteins Survival curves as a function of the number of srp's found to exceed their cutoff values are shown in FIG. 4. Positive (high) levels are the same as described in Example 3. Median followup was 74 months. Values below the X-axis show the number of patients at risk at the indicated time interval. Statistical significance (P-value) for pairwise comparisons between groups of patients separated according to the number of their high level srp's is given below.

|            | No srp+ | One srp+ | Two srp+ | Three srp+ | Four srp+ |
|------------|---------|----------|----------|------------|-----------|
| No srp+    |         |          |          |            |           |
| One srp+   | 0.6     |          |          |            |           |
| Two srp+   | 0.01    | 0.1      |          |            |           |
| Three srp+ | 0.0006  | 0.009    | 0.2      |            |           |
| Four srp+  | 0.0001  | 0.002    | 0.04     | 0.2        |           |

EXAMPLE 5 Standard for the Measurement of Stress Response Proteins

MCF-7 human breast cancer cells (originally obtained from the Michigan Cancer Foundation), ATCC HTB22 MCF-7 were cultured in Eagle's minimum essential medium (MEM) supplemented with 10 mM HEPES, 1% non-essential amino acids (Gibco), 2 mM L-glutamine (Gibco), 25 µg/ml gentamycin (Irvine Scientific), 6 ng/ml bovine insulin, and 5% calf serum (K. C. Biologicals). Sodium bicarbonate (0.2%) was added to adjust the final pH to approximately 7.2. Cells were allowed to grow at 37° C in an atmosphere containing 5% $CO_2$. Logarithmically growing MCF-7 cells close to confluency (75-100%) were harvested by a brief incubation with 1 mM EDTA in phosphate buffered saline (PBS). Cells were washed twice with PBS, and pelleted. Cell pellets were exposed to 5% sodium dodecyl sulfate (SDS), vortexed, and kept in a boiling water bath for 5 minutes, revortexed, and allowed to cool to room temperature for about 15 minutes. Clear supernatant was collected after spinning the tubes in a centrifuge. Protein concentration in the SDS extracts was determined by the BCA method (P. K. Smith et al., *Anal. Biochem.* 150, 76 (1985)). For the estimation of quantity of stress response proteins (srp's) in breast tumors by Western Blot, this SDS extract of MCF-7 human breast cancer cells was included in each gel at three concentrations (100 µg, 50 µg, and 25 µg protein, corresponding to 100, 50, and 25 units). The level of srp's in breast tumors was expressed in units relative to this standard.

The following examples, 6, 7, and 8, illustrate how stress response proteins could be analyzed by convenient kit means. The examples have not been tested using precisely the steps outlined but are illustrative of how such kits would be used.

EXAMPLE 6 This Example Illustrates the Steps that Could Be Used in a Western Blot Kit for Stress Response Protein Determination Mechanically pulverize the breast tumor specimen in liquid nitrogen to obtain a uniform distribution of tumor cells. Add 1 ml of 5% sodium dodecyl sulfate to 100 mg of tumor powder and vortex. Place the tube in a boiling water bath for 5 min and vortex. Centrifuge the tube at 13,000×g for 2 min and determine protein concentration in the clear supernatant using BCA reagents by mixing reagent A and B in a 50:1 ratio. Add 1 ml of this mixture to a 100 µl aliquot of test diluted sample or protein standard.

Incubate at room temperature for 1 hour, read absorbance at 562 nm, and calculate protein concentration by interpolation on the protein standard curve constructed based on the protein standard used in each experiment. Electrophorese 100 µg of solubilized tumor proteins on 10% polyacrylamide Laemmli gel under denaturing, reducing conditions. On each gel load the stress response proteins standard (vial 1) and tumor extracts from vial 2A and 2B as positive and negative controls. Electrically transfer proteins from the gel to nitroscreen filter (Towbin's procedure) using 200 mAmp current for 16 hours in the cold. Block nitroscreen by incubation for 1 hour at room temperature with 5% evaporated milk in PBS. Incubate nitroscreen with 1:50 fold dilution (prepared in 5% milk) of antibodies to stress-response proteins (vial 3) for 2 hours at room temperature with gentle shaking. Wash nitroscreen 3 times for 5 minutes each with phosphate buffered saline (PBS) on a shaker at room temperature. Incubate nitroscreen with 1:500 fold dilution (in 5% milk) of radioactive second antibody (vial 4) for 1 hour at room temperature with gentle shaking. Wash nitroscreen 3 times for 5 minutes each with PBS on a shaker at room temperature. Expose nitroscreen overnight to x-ray film at −70° C. Develop film and estimate the amount of four srp's in tumor specimen by densitometry of the relevant bands and calculation of ratios with the srp standard bands. High levels of srp's are defined as follows: $grp94 \geq 45$ units, $hsp90 \geq 32$ units; $hsp70 \geq 217$ units, and $hsp27 \geq 126$ units per 100 µg of tumor proteins.

EXAMPLE 7 This Example Illustrates the Steps That Could be Used in the Immunohistochemical Determination of Stress Response Proteins by a Kit Method Cut six 5-micron sections from the frozen OCT block of a breast tumor specimen and place each section on a separate adhesive-coated microscope slide provided with the kit. Air dry tissue sections for 30 minutes at room temperature (RT). Dip slides in −20° C. acetone for 5 minutes. (For formalin-fixed paraffin-embedded tumors, cut six 5-micron sections from the paraffin block. Bake at 60° C for 30 minutes in an oven. Dip slides in xylene 2-times for 5 minutes each. Place slides 2-times in 100% alcohol for 5 minutes each. The rest of the procedure is common to both frozen and fixed tumors.) Wash 2-times with PBS for 2 minutes each. Place slides for 30 minutes in PBS containing 0.1% $H_2O_2$ and 0.1% sodium azide. Wash 2-times with PBS for 2 minutes each. Cover tissue sections with 10% normal goat serum (vial 1) for 30 minutes at RT. Drain the solution and incubate four sections of the test tumor with four different monoclonal antibodies to srp's (vial 2A, 2B, 2C, 2D) at the dilution indicated on each vial. Similarly apply these antibodies to four control slides provided with the kit (control slides of breast tumor sections showing positive staining for srp's). Treat two remaining sections of the test tumor with the antibody negative controls (3A, 3B). Incubate all ten slides in a covered humidity chamber for 3 hours at RT. Wash 2-times with PBS for 2 minutes each. Incubate sections for 30 minutes at RT with appropriate biotinylated second antibody (4A or 4B) at the indicated dilution (sections treated with grp94 antibody or normal rat antibody control are treated with anti-rat second antibody (4A), while all other sections are treated with anti-mouse second antibody (4B)). Wash 2-times with PBS for 2 minutes each. Mix reagents from vial 5A and 5B as indicated on the vials to prepare avidin-biotin-peroxidase complex and apply to the sections for 30 minutes at RT. Wash 2-times with PBS for 2 minutes each. Incubate sections with diaminobenzidine (vial 6) dissolved as instructed in PBS containing 0.03% $H_2O_2$. Wash 2-times with PBS for 2 minutes each. Place slides in osmium tetroxide solution (vial 7) for 30 seconds. Wash with deionized water for 2 minutes and place in 0.5% methyl green for 2 minutes. Wash with deionized water for 2 minutes and dehydrate tissue by dipping in increasing concentrations of alcohol and finally in xylene. Cover with permount, place cover slip on the tissue and dry. View tissue sections under a microscope. Positive staining shows brown coloration in the cytoplasm.

EXAMPLE 8 This Example is Illustrative of Steps That Would be Utilized in an ELISA Kit Determination of Stress Response Proteins Coat 96-well microtiter places with a monoclonal antibody to srp (monoclonal antibodies to four different srp's are provided with the kit; vial 1A-1D). Incubate plates overnight at 4° C. with the antibody solution (100 µl/well) at 5 µg/ml in sodium carbonate buffer pH 9.6, or alternatively antibody-coated microtiter plates can be provided with a kit. Wash plates with PBS 3-times and incubate with 1% BSA in PBS for 1 hour at room temperature (RT). Wash with PBS 6-times. Dispense 100 µl/well test breast tumor cytosols, positive and negative controls (vial 2A, 2B) and standards (vial 3A-3D). Incubate at RT for 2 hours with gentle agitation. Wash with PBS 6-times. Incubate with 100 µl/well of a second set of anti-srp monoclonal antibodies labelled with horseradish peroxidase (vial 4A-4D) for 1 hour at RT. Wash with PBS 6-times. Add 100 µl/well of orthophenylene diamine (OPD) solution. Incubate in the dark at RT for 15 minutes. Stop reaction by adding 100 µl/well sulfuric acid and record absorbance at 490 nm. Construct standard curve by plotting absorbance against srp concentration. Calculate srp concentration in test cytosols by interpolation of their absorbance on the standard curve.

The literature citations appearing within the text of this application are hereby incorporated by reference into this application.

What is claimed is:

1. A method of determining likelihood of breast tumor recurrence in a lymph node-negative breast cancer patient, comprising:
   obtaining a tumor tissue sample from the patients;
   assaying said tumor tissue sample for the level of stress response proteins therein;
   obtaining for each stress response protein an overproduction level, said level being an amount above a measured level of the stress response protein produced by a standard cell line, wherein said measured level is a minimum amount statistically determined to be associated with tumor recurrence; and
   determining likelihood of breast tumor recurrence by comparing the measured level of the stress response proteins of the sample to the measured level of the standard cell line, wherein the overproduction level of at least two of said stress response proteins is associated with tumor recurrence in the patient.

2. The method of claim 1 wherein the stress response proteins are characterized as being proteins produced specifically in response to a cell stress.

3. The method recited in claim 1 wherein the stress response proteins are further characterized as having sizes of 94 kDa, 80 to 90 kDa, 68 to 74 kDa, or 18 to 30 kDa.

4. The method of claim 1 wherein at least one stress response protein is a glucose-regulated protein.

5. The method of claim 4 wherein the glucose regulated protein is further defined as being grp94.

6. The method of claim 1 wherein the stress response proteins comprise hsp27, hsp70, and hsp90.

7. The method of claim 1 wherein likelihood of breast tumor recurrence is positively correlated with a plurality of stress response proteins detected.

8. The method of claim 1 wherein tumor recurrence in the patient decreases with increasing number of overproduced tumor proteins in the tumor tissue wherein at least two of said proteins are overproduced.

9. A method of determining likelihood of tumor recurrence in a node negative breast tumor patient, comprising:
   obtaining a tumor tissue sample from the patient;
   assaying said tumor tissue sample to determine sample levels of at least two stress response proteins; and
   determining likelihood of breast tumor recurrence by comparing the measured level of the stress response proteins of the sample to measured level of the stress response proteins of a standard cell line, wherein the overproduction level of at least two of said stress response proteins is positively associated with tumor recurrence in the patient.

10. The method of claim 9 wherein the stress response proteins are further characterized as having sizes of 94 kDa, 80 to 90 Kda, 68 to 74 Kda or 18 or 30 Kda.

11. The method of claim 9 wherein at least two of the following stress response proteins are assessed: hsp27, hsp70, hsp90 and grp94.

12. The method of claim 9 wherein said comparing steps comprises comparing levels of the stress response protein in patient breast tumor samples with levels of corresponding stress response proteins in standard breast cancer cell line MCF-7, wherein a likelihood of tumor recurrence exists when at least two of the following are determined:
   patient sample grp94 is about 45 relative units compared with levels of grp94 found in the breast cancer cell line;
   patient sample hsp27 is between about 46 to abut 232 relative units compared with levels of hsp27 found in the breast cancer cell line;

patient sample hsp90 is between about 12 to about 59 relative units compared with levels of hsp90 found in the breast cancer cell line; and patient sample hsp70 is between about 120 to about 150 relative units compared with levels of hsp70 found in the breast caner cell line;

wherein one relative unit is the stress response protein level found in 1 μg of protein in the breast cancer cell line.

13. The method of claim 12 wherein optimal relative units correlating with tumor recurrence for each stress response protein relative to standard breast cancer cell line MCF-7 comprise:

a) at least 126 relative units for hsp27 in the patient sample;
   b) at least 217 relative units for hsp70 in the patient sample;
   c) at least 32 relative units for hsp90 in the patient sample; and
   d) at least 45 relative units for grp94 in the patient sample.

14. A kit useful for the Western Blot detection and measurement of tumor-associated stress response proteins, comprising:

a carrier being compartmentalized to receive one or more container means in close confinement therein;
   a first container means comprising a stress response protein standard;
   a second container means comprising a negative control breast tumor extract;
   a third container means comprising a positive control breast tumor extract;
   a fourth container means comprising primary antibodies directed against stress response proteins; and
   a fifth container means comprising labeled secondary antibodies directed against the primary antibodies.

15. The kit of claim 14 wherein the labeled secondary antibodies carry a radioisotope label, or a colorimetrically determinable label.

16. The kit of claim 14 wherein the antibodies directed against the stress response proteins are specific for grp94, hsp90, hsp70 and hsp27, respectively.

17. The kit of claim 14 wherein the stress response proteins standard, the positive and negative breast tumor extracts, and the antibodies directed against the stress response proteins are in lyophilized form.

18. A kit for the immunohistochemical determination of stress response proteins in tumor tissue comprising:

a carrier being compartmentalized to receive one or more container means in close confinement therein;
   a first container means comprising a normal serum from a first animal;
   a second container means comprising four separate vials each comprising four antibodies derived from a second or third animal, each antibody being directed to one of four different stress response proteins;
   a third container means comprising two separate vials, the first vial comprising a biotinylated antibody from a fourth animal specifically binding antibodies from the second animal, the second vial comprising a biotinylated antibody from a first, fourth, or fifth animal specifically binding antibodies from the third animal;
   a fourth container means comprising an antibody negative control obtained from the second animal;
   a fifth container means comprising an antibody negative control obtained from the third animal; and
   a sixth container means comprising four control slides with breast tumor sections.

19. The kit of claim 18 wherein the biotinylated second antibodies comprising the third container are anti-rat and anti-mouse biotinylated antibodies.

20. The kit of claim 18 wherein the antibody negative controls comprising the fourth and fifth container are normal rat and normal mouse IgG.

21. A kit useful for an ELISA determination of tumor associated stress response proteins comprising:

a carrier being compartmentalized to receive one or more container means in close confinement therein;
   a first container means comprising separate antibodies to at least two stress response proteins;
   a second container means comprising separate antibodies to at least two stress response proteins to which the antibodies of said first container are directed, coupled to horseradish peroxidase;
   a third container means comprising at least two stress response protein standards;
   a fourth container means comprising a positive breast tumor cytosol standard; and
   a fifth container means comprising a negative breast tumor cytosol standard.

22. The kit of claim 21 wherein the first container means comprises antibodies to stress response proteins grp94, hsp70, hsp27 and hsp90.

23. The kit of claim 21 wherein the second container means comprises four separate vials respectively containing antibodies to grp94, to hsp27, to hsp70, and to hsp90, each antibody being coupled with horseradish peroxidase.

24. The kit of claim 21 wherein the third container means comprises standards for hsp27, hsp90, hsp70 and grp94.

* * * * *

UNITED STATES PATENT AND TRADEMARK OFFICE
CERTIFICATE OF CORRECTION

PATENT NO. : 5,188,964
DATED : February 23, 1993
INVENTOR(S) : William L. McGuire, et al It is certified that error appears in the above-indentified patent and that said Letters Patent is hereby corrected as shown below:

On title page, item [75] add the following;

--Suzanne A. Fuqua-- column 21, line 66, delete "patients" and insert --patient--

Signed and Sealed this

Sixteenth Day of November, 1993

Attest:

BRUCE LEHMAN

Attesting Officer    Commissioner of Patents and Trademarks